(12) United States Patent
Al-Ali et al.

(10) Patent No.: US 10,991,135 B2
(45) Date of Patent: Apr. 27, 2021

(54) MEDICAL MONITORING ANALYSIS AND REPLAY INCLUDING INDICIA RESPONSIVE TO LIGHT ATTENUATED BY BODY TISSUE

(71) Applicant: Masimo Corporation, Irvine, CA (US)

(72) Inventors: Ammar Al-Ali, San Juan Capistrano, CA (US); Keith Ward Indorf, Riverside, CA (US); Swapnil Sudhir Harsule, Irvine, CA (US); Ronald Keith Rumbaugh, II, Mission Viejo, CA (US); Kun Han Kim, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/233,244

(22) Filed: Aug. 10, 2016

(65) Prior Publication Data
US 2017/0042488 A1  Feb. 16, 2017

Related U.S. Application Data

(60) Provisional application No. 62/203,792, filed on Aug. 11, 2015.

(51) Int. Cl.
*G06T 11/20* (2006.01)
*A61B 5/00* (2006.01)
(Continued)

(52) U.S. Cl.
CPC .......... *G06T 11/206* (2013.01); *A61B 5/0008* (2013.01); *A61B 5/0022* (2013.01);
(Continued)

(58) Field of Classification Search
CPC ...... G06T 11/206; A61B 5/0022; A61B 5/742
See application file for complete search history.

(56) References Cited

U.S. PATENT DOCUMENTS 4,960,128 A  10/1990  Gordon et al.
4,964,408 A  10/1990  Hink et al.
(Continued)

FOREIGN PATENT DOCUMENTS

CN  104042187  9/2014
EP  2871630 A1  5/2015
(Continued)

OTHER PUBLICATIONS

U.S. Appl. No. 62/183,732 of 2016/0379511, Dawson et al., filed Jun. 23, 2015.*
(Continued)

*Primary Examiner* — Michelle L Sams
(74) *Attorney, Agent, or Firm* — Knobbe, Martens, Olson & Bear, LLP

(57) ABSTRACT

The present disclosure includes a medical monitoring hub as the center of monitoring for a monitored patient. The hub is configured to receive and process a plurality of physiological parameters associated with the patient. The hub includes advanced analytical presentation views configured to provide timely, clinically-relevant, actionable information to care providers. In certain embodiments, the monitoring hub stores and is able to replay previously presented data reflective of the patient's condition.

33 Claims, 11 Drawing Sheets

(51) Int. Cl.
*A61B 5/0205* (2006.01)
*A61B 5/024* (2006.01)
*A61B 5/08* (2006.01)
*A61B 5/1455* (2006.01)

(52) U.S. Cl.
CPC ........ *A61B 5/0205* (2013.01); *A61B 5/02416* (2013.01); *A61B 5/08* (2013.01); *A61B 5/14551* (2013.01); *A61B 5/4839* (2013.01); *A61B 5/742* (2013.01); *A61B 5/746* (2013.01); *A61B 5/7445* (2013.01)

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |

(56) References Cited

U.S. PATENT DOCUMENTS

| | | |
|---|---|---|
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |

(56) References Cited

U.S. PATENT DOCUMENTS

| | | |
|---|---|---|
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,255,238 B2 | 8/2012 | Powell et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,288 B2 * | 10/2013 | Sugiura .............. A61B 5/055 382/131 |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |

(56) References Cited

U.S. PATENT DOCUMENTS

| | | |
|---|---|---|
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,856,729 B2 | 10/2014 | Moore et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,246,991 B2 | 1/2016 | Moore et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,400,874 B2 | 7/2016 | Powell et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,524,569 B2 | 12/2016 | Moore et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |

(56) References Cited

U.S. PATENT DOCUMENTS

| | | |
|---|---|---|
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 * | 10/2017 | Al-Ali .................... G01D 13/06 |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 9,996,667 B2 | 6/2018 | Moore et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |

(56) References Cited

U.S. PATENT DOCUMENTS

| | | |
|---|---|---|
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,284 B2 | 11/2019 | Al-Ali et al. |
| 10,463,340 B2 | 11/2019 | Telfort et al. |
| 10,470,695 B2 | 11/2019 | Al-Ali |
| 10,471,159 B1 | 11/2019 | Lapotko et al. |
| 10,478,107 B2 | 11/2019 | Kiani et al. |
| 10,503,379 B2 | 12/2019 | Al-Ali et al. |
| 10,505,311 B2 | 12/2019 | Al-Ali et al. |
| 10,512,436 B2 | 12/2019 | Muhsin et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0005703 A1* | 1/2009 | Fasciano .............. A61B 5/031 600/561 |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0131762 A1* | 5/2009 | Pelzek .................. G04C 13/02 600/301 |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0235782 A1 | 9/2010 | Powell et al. |
| 2010/0270257 A1 | 10/2010 | Wachman et al. |
| 2011/0001605 A1* | 1/2011 | Kiani .................... G06F 19/327 340/5.6 |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1* | 5/2011 | Kiani .................... G06F 19/327 600/300 |
| 2011/0118561 A1 | 5/2011 | Tari et al. |
| 2011/0118573 A1* | 5/2011 | McKenna ............. A61B 5/0205 600/323 |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0227927 A1* | 9/2011 | Garmon ................ B60W 50/14 345/440 |
| 2011/0230733 A1 | 9/2011 | Al-Ali |
| 2011/0237969 A1 | 9/2011 | Eckerbom et al. |
| 2011/0246235 A1 | 10/2011 | Powell et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0075103 A1* | 3/2012 | Powell ................. G06F 19/3418 340/573.1 |
| 2012/0078647 A1* | 3/2012 | Grassle ................ G06F 19/3406 705/2 |
| 2012/0088984 A1 | 4/2012 | Al-Ali et al. |
| 2012/0123231 A1 | 5/2012 | O'Reilly |
| 2012/0165629 A1 | 6/2012 | Merritt et al. |
| 2012/0171650 A1* | 7/2012 | Warner ................. A61B 5/04021 434/262 |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2013/0023775 A1 | 1/2013 | Lamego et al. |
| 2013/0030831 A1 | 1/2013 | Powell et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0162433 A1* | 6/2013 | Muhsin ................ G06F 17/30516 340/573.1 |
| 2013/0167111 A1 | 6/2013 | Moore et al. |
| 2013/0243021 A1 | 9/2013 | Siskavich |
| 2013/0253334 A1 | 9/2013 | Al-Ali et al. |
| 2013/0262730 A1* | 10/2013 | Al-Ali ................ A61M 16/0051 710/303 |
| 2013/0267804 A1 | 10/2013 | Al-Ali |
| 2013/0271469 A1 | 10/2013 | Moore et al. |
| 2013/0271470 A1 | 10/2013 | Moore et al. |
| 2013/0274572 A1 | 10/2013 | Al-Ali et al. |
| 2013/0275145 A1 | 10/2013 | Moore et al. |
| 2013/0275151 A1 | 10/2013 | Moore et al. |
| 2013/0275152 A1 | 10/2013 | Moore et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |

(56) References Cited

U.S. PATENT DOCUMENTS

| | | |
|---|---|---|
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0345921 A1 | 12/2013 | Al-Ali et al. |
| 2014/0012100 A1 | 1/2014 | Al-Ali et al. |
| 2014/0019901 A1 | 1/2014 | Powell et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0073888 A1 | 3/2014 | Sethi et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0136089 A1* | 5/2014 | Hranac ............... G08G 1/0962 701/118 |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194766 A1 | 7/2014 | Al-Ali et al. |
| 2014/0213864 A1 | 7/2014 | Abdul-Hafiz et al. |
| 2014/0249854 A1 | 9/2014 | Moore et al. |
| 2014/0249855 A1 | 9/2014 | Moore et al. |
| 2014/0249856 A1 | 9/2014 | Moore et al. |
| 2014/0249857 A1 | 9/2014 | Moore et al. |
| 2014/0249858 A1 | 9/2014 | Moore et al. |
| 2014/0266790 A1 | 9/2014 | Al-Ali et al. |
| 2014/0275808 A1 | 9/2014 | Poeze et al. |
| 2014/0275819 A1* | 9/2014 | Kassem ............... A61B 5/743 600/301 |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0278486 A1 | 9/2014 | Moore et al. |
| 2014/0278487 A1 | 9/2014 | Moore et al. |
| 2014/0278488 A1 | 9/2014 | Moore et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2014/0372518 A1 | 12/2014 | Moore et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0025406 A1 | 1/2015 | Al-Ali |
| 2015/0032029 A1 | 1/2015 | Al-Ali et al. |
| 2015/0035959 A1* | 2/2015 | Amble ............... A61B 8/565 348/74 |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0088549 A1 | 3/2015 | Moore et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1* | 4/2015 | Al-Ali ............... A61B 5/14552 600/364 |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0367136 A1* | 12/2015 | Rondoni ............... A61N 1/37217 607/42 |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |

(56) References Cited

U.S. PATENT DOCUMENTS

| | | | |
|---|---|---|---|
| 2016/0379511 A1* | 12/2016 | Dawson | G09B 7/08 434/362 |
| 2017/0007134 A1 | 1/2017 | Al-Ali et al. | |
| 2017/0007190 A1 | 1/2017 | Al-Ali et al. | |
| 2017/0007198 A1 | 1/2017 | Al-Ali et al. | |
| 2017/0014084 A1 | 1/2017 | Al-Ali et al. | |
| 2017/0024748 A1 | 1/2017 | Haider | |
| 2017/0027456 A1 | 2/2017 | Kinast et al. | |
| 2017/0042488 A1 | 2/2017 | Muhsin | |
| 2017/0055851 A1 | 3/2017 | Al-Ali | |
| 2017/0055882 A1 | 3/2017 | Al-Ali et al. | |
| 2017/0055887 A1 | 3/2017 | Al-Ali | |
| 2017/0055896 A1 | 3/2017 | Al-Ali et al. | |
| 2017/0079594 A1 | 3/2017 | Telfort et al. | |
| 2017/0086723 A1 | 3/2017 | Al-Ali et al. | |
| 2017/0143281 A1 | 5/2017 | Olsen | |
| 2017/0147774 A1 | 5/2017 | Kiani | |
| 2017/0156620 A1 | 6/2017 | Al-Ali et al. | |
| 2017/0173632 A1 | 6/2017 | Al-Ali | |
| 2017/0187146 A1 | 6/2017 | Kiani et al. | |
| 2017/0188919 A1 | 7/2017 | Al-Ali et al. | |
| 2017/0196464 A1 | 7/2017 | Jansen et al. | |
| 2017/0196470 A1 | 7/2017 | Lamego et al. | |
| 2017/0202490 A1 | 7/2017 | Al-Ali et al. | |
| 2017/0224262 A1 | 8/2017 | Al-Ali | |
| 2017/0228516 A1 | 8/2017 | Sampath et al. | |
| 2017/0245790 A1 | 8/2017 | Al-Ali et al. | |
| 2017/0249435 A1 | 8/2017 | Lancelot | |
| 2017/0251974 A1 | 9/2017 | Shreim et al. | |
| 2017/0251975 A1 | 9/2017 | Shreim et al. | |
| 2017/0258403 A1 | 9/2017 | Abdul-Hafiz et al. | |
| 2017/0311851 A1 | 11/2017 | Schurman et al. | |
| 2017/0311891 A1 | 11/2017 | Kiani et al. | |
| 2017/0325728 A1 | 11/2017 | Al-Ali et al. | |
| 2017/0332976 A1 | 11/2017 | Al-Ali et al. | |
| 2017/0340293 A1 | 11/2017 | Al-Ali et al. | |
| 2017/0360310 A1 | 12/2017 | Kiani et al. | |
| 2017/0367632 A1 | 12/2017 | Al-Ali et al. | |
| 2018/0008146 A1 | 1/2018 | Al-Ali et al. | |
| 2018/0014752 A1 | 1/2018 | Al-Ali et al. | |
| 2018/0028124 A1 | 2/2018 | Al-Ali et al. | |
| 2018/0055385 A1 | 3/2018 | Al-Ali | |
| 2018/0055390 A1 | 3/2018 | Kiani et al. | |
| 2018/0055430 A1 | 3/2018 | Diab et al. | |
| 2018/0064381 A1 | 3/2018 | Shakespeare et al. | |
| 2018/0069776 A1 | 3/2018 | Lamego et al. | |
| 2018/0082767 A1 | 3/2018 | Al-Ali et al. | |
| 2018/0085068 A1 | 3/2018 | Telfort | |
| 2018/0087937 A1 | 3/2018 | Al-Ali et al. | |
| 2018/0103874 A1 | 4/2018 | Lee et al. | |
| 2018/0103905 A1 | 4/2018 | Kiani | |
| 2018/0110478 A1 | 4/2018 | Al-Ali | |
| 2018/0116575 A1 | 5/2018 | Perea et al. | |
| 2018/0125368 A1 | 5/2018 | Lamego et al. | |
| 2018/0125430 A1 | 5/2018 | Al-Ali et al. | |
| 2018/0125445 A1 | 5/2018 | Telfort et al. | |
| 2018/0130325 A1 | 5/2018 | Kiani et al. | |
| 2018/0132769 A1 | 5/2018 | Weber et al. | |
| 2018/0132770 A1 | 5/2018 | Lamego | |
| 2018/0146901 A1 | 5/2018 | Al-Ali et al. | |
| 2018/0146902 A1 | 5/2018 | Kiani et al. | |
| 2018/0153442 A1 | 6/2018 | Eckerbom et al. | |
| 2018/0153447 A1 | 6/2018 | Al-Ali et al. | |
| 2018/0153448 A1 | 6/2018 | Weber et al. | |
| 2018/0161499 A1 | 6/2018 | Al-Ali et al. | |
| 2018/0168491 A1 | 6/2018 | Al-Ali et al. | |
| 2018/0174679 A1 | 6/2018 | Sampath et al. | |
| 2018/0174680 A1 | 6/2018 | Sampath et al. | |
| 2018/0182484 A1 | 6/2018 | Sampath et al. | |
| 2018/0184917 A1 | 7/2018 | Kiani | |
| 2018/0192953 A1 | 7/2018 | Shreim et al. | |
| 2018/0192955 A1 | 7/2018 | Al-Ali et al. | |
| 2018/0199871 A1 | 7/2018 | Pauley et al. | |
| 2018/0206795 A1 | 7/2018 | Al-Ali | |
| 2018/0206815 A1 | 7/2018 | Telfort | |
| 2018/0213583 A1 | 7/2018 | Al-Ali | |
| 2018/0214031 A1 | 8/2018 | Kiani et al. | |
| 2018/0214090 A1 | 8/2018 | Al-Ali et al. | |
| 2018/0218792 A1 | 8/2018 | Muhsin et al. | |
| 2018/0225960 A1 | 8/2018 | Al-Ali et al. | |
| 2018/0238718 A1 | 8/2018 | Dalvi | |
| 2018/0242853 A1 | 8/2018 | Al-Ali | |
| 2018/0242921 A1 | 8/2018 | Muhsin et al. | |
| 2018/0242924 A1 | 8/2018 | Barker et al. | |
| 2018/0242926 A1 | 8/2018 | Muhsin et al. | |
| 2018/0247353 A1 | 8/2018 | Al-Ali et al. | |
| 2018/0247712 A1 | 8/2018 | Muhsin et al. | |
| 2018/0249933 A1 | 9/2018 | Schurman et al. | |
| 2018/0253947 A1 | 9/2018 | Muhsin et al. | |
| 2018/0256087 A1 | 9/2018 | Al-Ali et al. | |
| 2018/0256113 A1 | 9/2018 | Weber et al. | |
| 2018/0285094 A1 | 10/2018 | Housel et al. | |
| 2018/0289325 A1 | 10/2018 | Poeze et al. | |
| 2018/0289337 A1 | 10/2018 | Al-Ali et al. | |
| 2018/0296161 A1 | 10/2018 | Shreim et al. | |
| 2018/0300919 A1 | 10/2018 | Muhsin et al. | |
| 2018/0310822 A1 | 11/2018 | Indorf et al. | |
| 2018/0310823 A1 | 11/2018 | Al-Ali et al. | |
| 2018/0317826 A1 | 11/2018 | Muhsin | |
| 2018/0317841 A1 | 11/2018 | Novak, Jr. | |
| 2018/0333055 A1 | 11/2018 | Lamego et al. | |
| 2018/0333087 A1 | 11/2018 | Al-Ali | |
| 2019/0000317 A1 | 1/2019 | Muhsin et al. | |
| 2019/0000362 A1 | 1/2019 | Kiani et al. | |
| 2019/0015023 A1 | 1/2019 | Monfre | |
| 2019/0021638 A1 | 1/2019 | Al-Ali et al. | |
| 2019/0029574 A1 | 1/2019 | Schurman et al. | |
| 2019/0029578 A1 | 1/2019 | Al-Ali et al. | |
| 2019/0038143 A1 | 2/2019 | Al-Ali | |
| 2019/0058280 A1 | 2/2019 | Al-Ali et al. | |
| 2019/0058281 A1 | 2/2019 | Al-Ali et al. | |
| 2019/0069813 A1 | 3/2019 | Al-Ali | |
| 2019/0069814 A1 | 3/2019 | Al-Ali | |
| 2019/0076028 A1 | 3/2019 | Al-Ali et al. | |
| 2019/0082979 A1 | 3/2019 | Al-Ali et al. | |
| 2019/0090748 A1 | 3/2019 | Al-Ali | |
| 2019/0090760 A1 | 3/2019 | Kinast et al. | |
| 2019/0090764 A1 | 3/2019 | Al-Ali | |
| 2019/0104973 A1 | 4/2019 | Poeze et al. | |
| 2019/0110719 A1 | 4/2019 | Poeze et al. | |
| 2019/0117070 A1 | 4/2019 | Muhsin et al. | |
| 2019/0117139 A1 | 4/2019 | Al-Ali et al. | |
| 2019/0117140 A1 | 4/2019 | Al-Ali et al. | |
| 2019/0117141 A1 | 4/2019 | Al-Ali | |
| 2019/0117930 A1 | 4/2019 | Al-Ali | |
| 2019/0122763 A1 | 4/2019 | Sampath et al. | |
| 2019/0133525 A1 | 5/2019 | Al-Ali et al. | |
| 2019/0142283 A1 | 5/2019 | Lamego et al. | |
| 2019/0142344 A1 | 5/2019 | Telfort et al. | |
| 2019/0150800 A1 | 5/2019 | Poeze et al. | |
| 2019/0150856 A1 | 5/2019 | Kiani et al. | |
| 2019/0167161 A1 | 6/2019 | Al-Ali et al. | |
| 2019/0175019 A1 | 6/2019 | Al-Ali et al. | |
| 2019/0200941 A1 | 7/2019 | Chandran et al. | |
| 2019/0239787 A1 | 8/2019 | Pauley et al. | |
| 2019/0320906 A1 | 10/2019 | Olsen | |
| 2019/0374139 A1 | 12/2019 | Kiani et al. | |
| 2019/0374173 A1 | 12/2019 | Kiani et al. | |
| 2019/0374713 A1 | 12/2019 | Kiani et al. | |
| 2020/0021930 A1 | 1/2020 | Iswanto et al. | |
| 2020/0060869 A1 | 2/2020 | Telfort et al. | |
| 2020/0111552 A1 | 4/2020 | Ahmed | |
| 2020/0113435 A1 | 4/2020 | Muhsin | |
| 2020/0113488 A1 | 4/2020 | Al-Ali et al. | |
| 2020/0113496 A1 | 4/2020 | Scruggs et al. | |
| 2020/0113497 A1 | 4/2020 | Triman et al. | |
| 2020/0113520 A1 | 4/2020 | Abdul-Hafiz et al. | |
| 2020/0138288 A1 | 5/2020 | Al-Ali et al. | |
| 2020/0138368 A1 | 5/2020 | Kiani et al. | |
| 2020/0163597 A1 | 5/2020 | Dalvi et al. | |
| 2020/0196877 A1 | 6/2020 | Vo et al. | |
| 2020/0253474 A1 | 8/2020 | Muhsin et al. | |
| 2020/0253544 A1 | 8/2020 | Belur Nagaraj et al. | |
| 2020/0275841 A1 | 9/2020 | Telfort et al. | |

(56) References Cited

U.S. PATENT DOCUMENTS

| | | |
|---|---|---|
| 2020/0288983 A1 | 9/2020 | Telfort et al. |
| 2020/0321793 A1 | 10/2020 | Ai-Ali et al. |
| 2020/0329983 A1 | 10/2020 | Ai-Ali et al. |
| 2020/0329984 A1 | 10/2020 | Ai-Ali et al. |
| 2020/0329993 A1 | 10/2020 | Ai-Ali et al. |
| 2020/0330037 A1 | 10/2020 | Ai-Ali et al. |

FOREIGN PATENT DOCUMENTS

| | | |
|---|---|---|
| GB | 2505890 A | 3/2014 |
| JP | 2010-194306 | 9/2010 |
| JP | 2014-150845 | 8/2014 |
| JP | 2015-123228 | 7/2015 |
| WO | WO 2014/110280 | 7/2014 |
| WO | WO 2015054665 A1 | 4/2015 |
| WO | WO 2017/027621 | 2/2017 |

OTHER PUBLICATIONS

Chandoo.org, "Use Indexed charts when understanding change [Charting Techniques]", Oct. 9, 2012, https://chandoo.org/wp/2012/10/09/indexed-charts-in-excel/.*
Mathwavecom, "Distribution Fitting", Feb. 20, 2008, http://www.mathwave.com/articles/distribution-fitting-graphs.html.*
Purplemath.com, "Box-and Whisker Plots: Quartiles, Boxes, and Whiskers", Jan. 22, 2013, https://web.archive.org/web/20130122015633/http://www.purplemath.com:80/modules/boxwhisk.htm.*
fusioncharts.com, "Heat Map Chart", Aug. 11, 2011, https://www.fusioncharts.com/chart-primers/heat-map-chart/.*
International Search Report and Written Opinion in corresponding International Patent Application No. PCT/US2016/046400, dated Nov. 2, 2016, in 13 pages.

\* cited by examiner

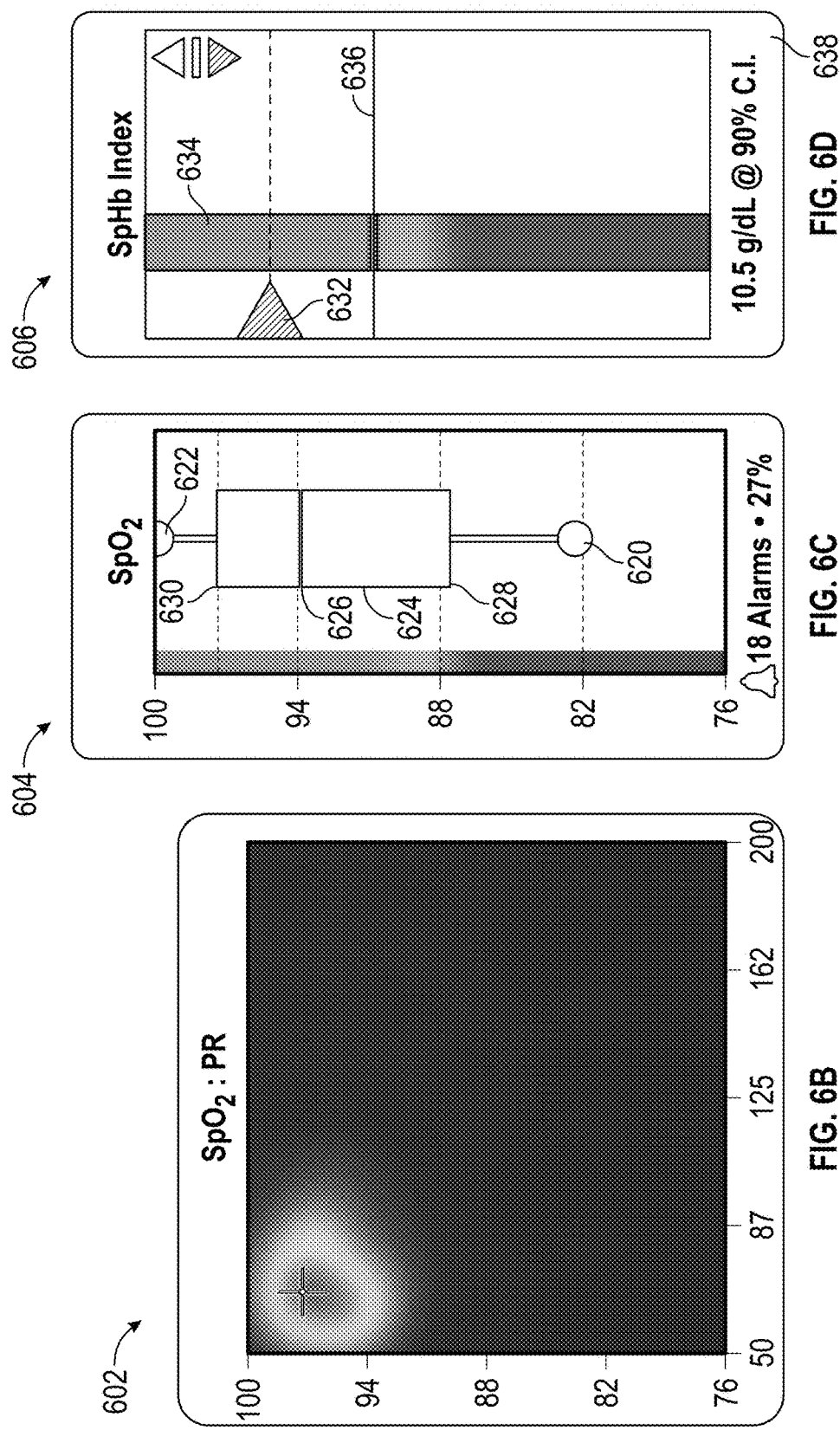

MEDICAL MONITORING ANALYSIS AND REPLAY INCLUDING INDICIA RESPONSIVE TO LIGHT ATTENUATED BY BODY TISSUE

INCORPORATION BY REFERENCE TO ANY PRIORITY APPLICATIONS

The present application claims priority benefit under 35 U.S.C. § 119(e) to U.S. Provisional Application No. 62/203,792, filed Aug. 11, 2015, which is hereby incorporated by reference in its entirety herein. Any and all applications for which a foreign or domestic priority claim is identified in the Application Data Sheet as filed with the present application are hereby incorporated by reference under 37 CFR 1.57.

FIELD

The present disclosure relates generally to a patient monitor and medical data communication hub and specifically to a patient monitor including display elements for presenting measurement information, often over a time period, to a caregiver.

BACKGROUND

Today's patient monitoring environments are crowded with sophisticated and often electronic medical devices servicing a wide variety of monitoring and treatment endeavors for a given patient. Generally, many if not all of the devices are from differing manufactures, and many may be portable devices. The devices may not communicate with one another and each may include its own control, display, alarms, configurations and the like. Complicating matters, caregivers often desire to associate all types of measurement and data from these devices with a specific patient. Patient information entry often occurs at each device. Sometimes, the disparity in devices leads to a need to simply print and store paper from each device in a patient's file for caregiver review.

Thus, while the electronic collection of physiological data associated with the patient's condition has increased, the ability to synthesize the collected patient data into timely, clinically-relevant, actionable information remains a challenge.

SUMMARY

Based on at least the foregoing, a solution is needed that coordinates the various medical devices treating or monitoring a patient and the measurement data being generated by such devices. Embodiments of such a solution may include a medical hub that presents, via graphical display, a variety of analytical presentation views that deliver to the caregiver easily-seen, intuitive, visual indications of the status and condition of the patient being monitored. In an embodiment, the analytical graphical views may advantageously be replayed for analysis of critical events in the patient's care, or to simply review the patient's physiological activity over a period of time. In an embodiment, the replays of several physiological parameters may be played synchronously, providing a broad perspective of the patient's historical activity.

According to an embodiment of the present disclosure, a medical monitoring hub is configured to monitor physiological parameters of a patient. The hub includes a first communication port configured to receive a first signal indicative a first physiological parameter associated with the patient. The monitor also includes a display configured to present analytical presentation views to the user. The monitor includes at least one processor configured to process the received first signal and to cause a first view to be presented on at least a portion of the display. The first view is adapted to present first data indicative of the first physiological parameter collected over a first period of time. The hub includes a storage device configured to store the presented first data, and the processor is further configured to replay the stored first data on the display.

In certain embodiments of the present disclosure, various analytical presentation views are disclosed to help clinicians easily and intuitively interpret the patient data that is received by the monitoring hub. Heat maps are disclosed which provide a two-dimensional graphical representation of a relationship between two measured physiological parameters over a specified period of time. Advantageously, heat maps use color to identify areas in the graph where the data is concentrated. For example, areas where the data is highly concentrated can be presented in a first color (e.g., red), while areas in which the data is less highly concentrated can be presented in a second color (e.g., blue).

Also disclosed are box-and-whisker plots which visually present the range of physiological parameter measurements received over a specified or pre-determined period of time. Additionally, the boundaries of the quartiles in which the data lies are presented by the box-and-whisker plots. Advantageously, the box-and-whisker plot readily presents to the user the degree of spread, or dispersion of the measured data, as well as the skewness in the data, including outlier measurements.

Index box views are disclosed as well. An index box view presents a current measured state of a physiological parameter relative to ranges identified as, for example, acceptable, cautionary, and emergent, using colors and other visual cues to readily indicate the measured state of the patient.

The present disclosure also describes distribution analytical presentation views which present a statistical distribution (e.g., a Gaussian distribution) of physiological parameter measurements over a specified or pre-defined period of time. Similarly, the present disclosure describes histogram analytical presentation views which provide yet another graphical representation of a measured physiological parameter data. A histogram represents an estimate of the statistical (or probability) distribution of a continuous variable, such as a continuously measured physiological parameter. Thus, rather than providing a statistical distribution (i.e., a probabilistic model) that best fits or corresponds to the measured data, the histogram reflects the actual measured data collected.

The present disclosure also includes gauge-histogram analytical presentation views, which provide a combination of analog, digital, and histogram display indicia. Advantageously, the gauge-histogram analytical presentation view provides to the clinician a substantial amount of information related to the measured physiological parameter in an intuitive and visually accessible format.

In use, the clinician is provided a great deal of flexibility in arranging and configuring the disclosed analytical presentation views of the present disclosure. Thus, the clinician is provided a monitoring environment that can be customized to the clinician's and/or patient's specific needs.

For purposes of summarizing the disclosure, certain aspects, advantages and novel features are discussed herein. It is to be understood that not necessarily all such aspects, advantages or features will be embodied in any particular embodiment of the invention, and an artisan would recognize from the disclosure herein a myriad of combinations of such aspects, advantages or features.

BRIEF DESCRIPTION OF THE DRAWINGS

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

FIG. 1A illustrates the hub with an exemplary docked portable patient monitor; FIG. 1B illustrates the hub with a set of medical ports and a noninvasive blood pressure input; and FIG. 1C illustrates the hub with various exemplary temperature sensors attached thereto, all according to various embodiments of the disclosure.

FIG. 6B illustrates a heat map analytical presentation view according to an embodiment of the disclosure.

FIG. 6C illustrates a box-and-whisker analytical presentation view according to an embodiment of the disclosure.

FIG. 6D illustrates an index analytical presentation view according to an embodiment of the disclosure.

Figure 1A:
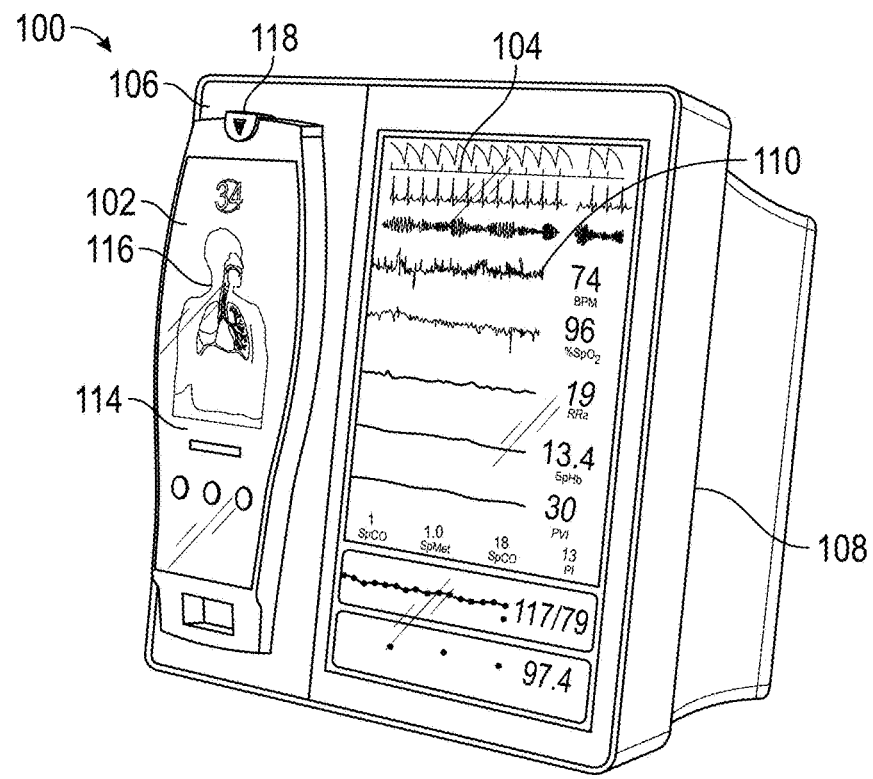
FIGS. 1A-1C illustrate perspective views of an exemplary medical monitoring hub according to an embodiment of the disclosure. For example.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

The present disclosure relates to a medical monitoring hub configured to be the center of monitoring activity for a given patient. In an embodiment, the hub comprises a large easily readable display, such as an about ten (10) inch display dominating the majority of real estate on a front face of the hub. The display could be much larger or much smaller depending upon design constraints. However, for portability and current design goals, the preferred display is roughly sized proportional to the vertical footprint of one of a dockable portable patient monitor. Other considerations are recognizable from the disclosure herein by those in the art.

Configurable Replay Display

In an embodiment, the display is configurable by dragging and dropping gestures to populate the display with elements a caregiver prefers to view for a particular user. The elements may include some or all of a heat map, a box-and-whisker plot, a distribution plot, a histogram, an analog gage, and an analog gage combined with a histogram. Once configured, the hub processor may allow for the replay of selected measurement data, data responsive to the measurement data, or combinations of measurement data over a selected or default time period at a selected or default display rate. Advantageously, such configuration and replay provide a powerful tool for a caregiver to review the patient's condition over virtually any period of time desired.

Monitoring Hub

The display provides measurement data for a wide variety of monitored parameters for the patient under observation in numerical or graphic form, and in various embodiments, is automatically configured based on the type of data and information being received at the hub. In an embodiment, the hub is moveable, portable, and mountable so that it can be positioned to convenient areas within a caregiver environment. For example, the hub is collected within a singular housing.

In an embodiment, the hub may advantageously receive data from a portable patient monitor while docked or undocked from the hub. Typical portable patient monitors, such as oximeters or co-oximeters can provide measurement data for a large number of physiological parameters derived from signals output from optical and/or acoustic sensors, electrodes, or the like. The physiological parameters include, but not limited to oxygen saturation, carboxy hemoglobin, methemoglobin, total hemoglobin, glucose, pH, bilirubin, fractional saturation, pulse rate, respiration rate, components of a respiration cycle, indications of perfusion including perfusion index, signal quality and/or confidences, plethysmograph data, indications of wellness or wellness indexes or other combinations of measurement data, audio information responsive to respiration, ailment identification or diagnosis, blood pressure, patient and/or measurement site temperature, depth of sedation, organ or brain oxygenation, hydration, measurements responsive to metabolism, combinations of the same or the like, to name a few. In other embodiments, the hub may output data sufficient to accomplish closed-loop drug administration in combination with infusion pumps or the like.

In an embodiment, the hub communicates with other devices in a monitoring environment that are interacting with the patient in a number of ways. For example, the hub advantageously receives serial data from other devices without necessitating their reprogramming or that of the hub. Such other devices include pumps, ventilators, all manner of monitors monitoring any combination of the foregoing parameters, ECG/EEG/EKG devices, electronic patient beds, and the like. Moreover, the hub advantageously receives channel data from other medical devices without necessitating their reprogramming or that of the hub. When a device communicates through channel data, the hub may advantageously alter the large display to include measurement information from that device. Additionally, the hub accesses nurse call systems to ensure that nurse call situations from the device are passed to the appropriate nurse call system.

The hub also communicates with hospital systems to advantageously associate incoming patient measurement and treatment data with the patient being monitored. For example, the hub may communicate wirelessly or otherwise to a multi-patient monitoring system, such as a server or collection of servers, which in turn many communicate with a caregiver's data management systems, such as, for example, an Admit, Discharge, Transfer ("ADT") system and/or an Electronic Medical Records ("EMR") system. The hub advantageously associates the data flowing through it with the patient being monitored thereby providing the electronic measurement and treatment information to be passed to the caregiver's data management systems without the caregiver associating each device in the environment with the patient.

In an embodiment, the hub advantageously includes a reconfigurable and removable docking station. The docking station may dock additional layered docking stations to adapt to different patient monitoring devices. Additionally, the docking station itself is modularized so that it may be removed if the primary dockable portable patient monitor changes its form factor. Thus, the hub is flexible in how its docking station is configured.

In an embodiment, the hub includes a large memory for storing some or all of the data it receives, processes, and/or associates with the patient, and/or communications it has with other devices and systems. Some or all of the memory may advantageously comprise removable SD memory.

The hub communicates with other devices through at least (1) the docking station to acquire data from a portable monitor, (2) innovative universal medical connectors to acquire channel data, (3) serial data connectors, such as RJ ports to acquire output data, (4) Ethernet, USB, and nurse call ports, (5) Wireless devices to acquire data from a portable monitor, (6) other wired or wireless communication mechanisms known to an artisan. The universal medical connectors advantageously provide optional electrically isolated power and communications, are designed to be smaller in cross section than isolation requirements. The connectors and the hub communicate to advantageously translate or configure data from other devices to be usable and displayable for the hub. In an embodiment, a software developers kit ("SDK") is provided to a device manufacturer to establish or define the behavior and meaning of the data output from their device. When the output is defined, the definition is programmed into a memory residing in the cable side of the universal medical connector and supplied as an original equipment manufacturer ("OEM") to the device provider. When the cable is connected between the device and the hub, the hub understands the data and can use it for display and processing purposes without necessitating software upgrades to the device or the hub. In an embodiment, the hub can negotiate the schema and even add additional compression and/or encryption. Through the use of the universal medical connectors, the hub organizes the measurement and treatment data into a single display and alarm system effectively and efficiently bringing order to the monitoring environment.

As the hub receives and tracks data from other devices according to a channel paradigm, the hub may advantageously provide processing to create virtual channels of patient measurement or treatment data. In an embodiment, a virtual channel may comprise a non-measured parameter that is, for example, the result of processing data from various measured or other parameters. An example of such a parameter includes a wellness indicator derived from various measured parameters that give an overall indication of the wellbeing of the monitored patient. An example of a wellness parameter is disclosed in U.S. patent application Ser. Nos. 13/269,296, 13/371,767 and 12/904,925, by the assignee of the present disclosure and incorporated by reference herein. By organizing data into channels and virtual channels, the hub may advantageously time-wise synchronize incoming data and virtual channel data.

The hub also receives serial data through serial communication ports, such as RJ connectors. The serial data is associated with the monitored patient and passed on to the multi-patient server systems and/or caregiver backend systems discussed above. Through receiving the serial data, the caregiver advantageously associates devices in the caregiver environment, often from varied manufactures, with a particular patient, avoiding a need to have each individual device associated with the patient and possible communicating with hospital systems. Such association is vital as it reduces caregiver time spent entering biographic and demographic information into each device about the patient. Moreover, in an embodiment, through the SDK the device manufacturer may advantageously provide information associated with any measurement delay of their device, thereby further allowing the hub to advantageously time-wise synchronize serial incoming data and other data associated with the patient.

In an embodiment, when a portable patient monitor is docked, and it includes its own display, the hub effectively increases its display real estate. For example, in an embodiment, the portable patient monitor may simply continue to display its measurement and/or treatment data, which may be now duplicated on the hub display, or the docked display, may alter its display to provide additional information. In an embodiment, the docked display, when docked, presents anatomical graphical data of, for example, the heart, lungs, organs, the brain, or other body parts being measured and/or treated. The graphical data may advantageously animate similar to and in concert with the measurement data. For example, lungs may inflate in approximate correlation to the measured respiration rate and/or the determined inspiration/expiration portions of a respiration cycle, the heart may beat according to the pulse rate, may beat generally along understood actual heart contraction patterns, the brain may change color or activity based on varying depths of sedation, or the like. In an embodiment, when the measured parameters indicate a need to alert a caregiver, a changing severity in color may be associated with one or more displayed graphics, such as the heart, lungs, brain, organs, circulatory system or portions thereof, respiratory system or portions thereof, other body parts or the like. In still other embodiments, the body portions may include animations on where, when or how to attach measurement devices.

The hub may also advantageously overlap parameter displays to provide additional visual information to the caregiver. Such overlapping may be user definable and configurable. The display may also incorporate analog-appearing icons or graphical indicia.

In the interest of clarity, not all features of an actual implementation are described in this specification. An artisan will of course appreciate that in the development of any such actual implementation (as in any development project), numerous implementation-specific decisions must be made to achieve a developers' specific goals and sub-goals, such as compliance with system- and business-related constraints, which will vary from one implementation to another. Moreover, it will be appreciated that such a development effort might be complex and time-consuming, but would nevertheless be a routine undertaking of device engineering for those of ordinary skill having the benefit of this disclosure.

To facilitate a complete understanding of the disclosure, the remainder of the detailed description describes the disclosure with reference to the drawings, wherein like reference numbers are referenced with like numerals throughout.

Embodiments of Monitoring Hub

FIG. 1A illustrates a perspective view of an exemplary medical monitoring hub 100, which may also be referred to herein as a monitor 100, with an exemplary docked portable patient monitor 102 according to an embodiment of the disclosure. The hub 100 includes a display 104, and a docking station 106, which in an embodiment is configured to mechanically and electrically mate with the portable patient monitor 102, each housed in a movable, mountable and portable housing 108. The housing 108 includes a generally upright inclined shape configured to rest on a horizontal flat surface, although the housing 108 can be affixed in a wide variety of positions and mountings and comprise a wide variety of shapes and sizes.

In an embodiment, the display 104 may present a wide variety of measurement and/or treatment data in numerical, graphical, waveform, or other display indicia 110. In an embodiment, the display 104 occupies much of a front face of the housing 108, although an artisan will appreciate the display 104 may comprise a tablet or tabletop horizontal configuration, a laptop-like configuration or the like. Other embodiments may include communicating display information and data to a table computer, smartphone, television, or any display system recognizable to an artisan. The upright inclined configuration of FIG. 1A presents display information to a caregiver in an easily viewable manner.

Figure 1B:
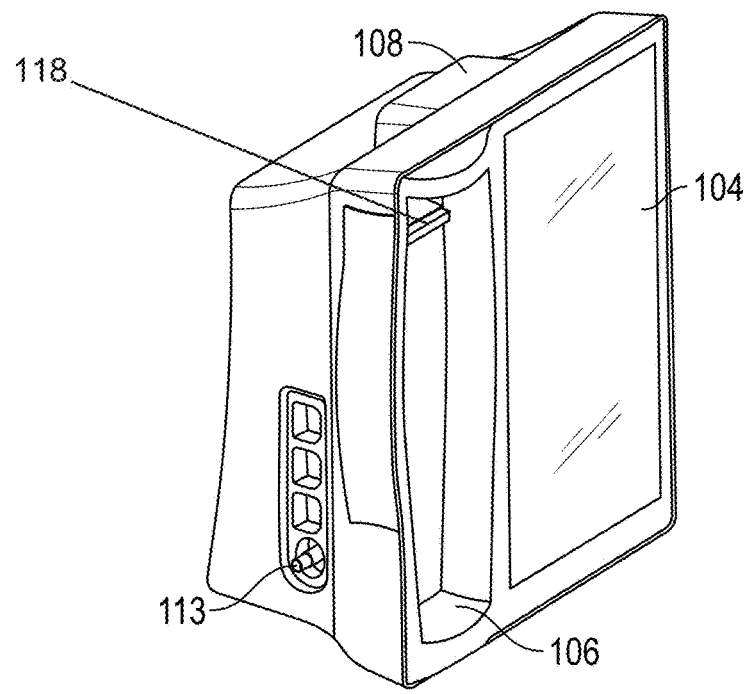

FIG. 1B shows a perspective side view of an embodiment of the hub 100 including the housing 108, the display 104, and the docking station 106 without a portable monitor docked. Also shown is a connector for noninvasive blood pressure 113.

Figure 1C:
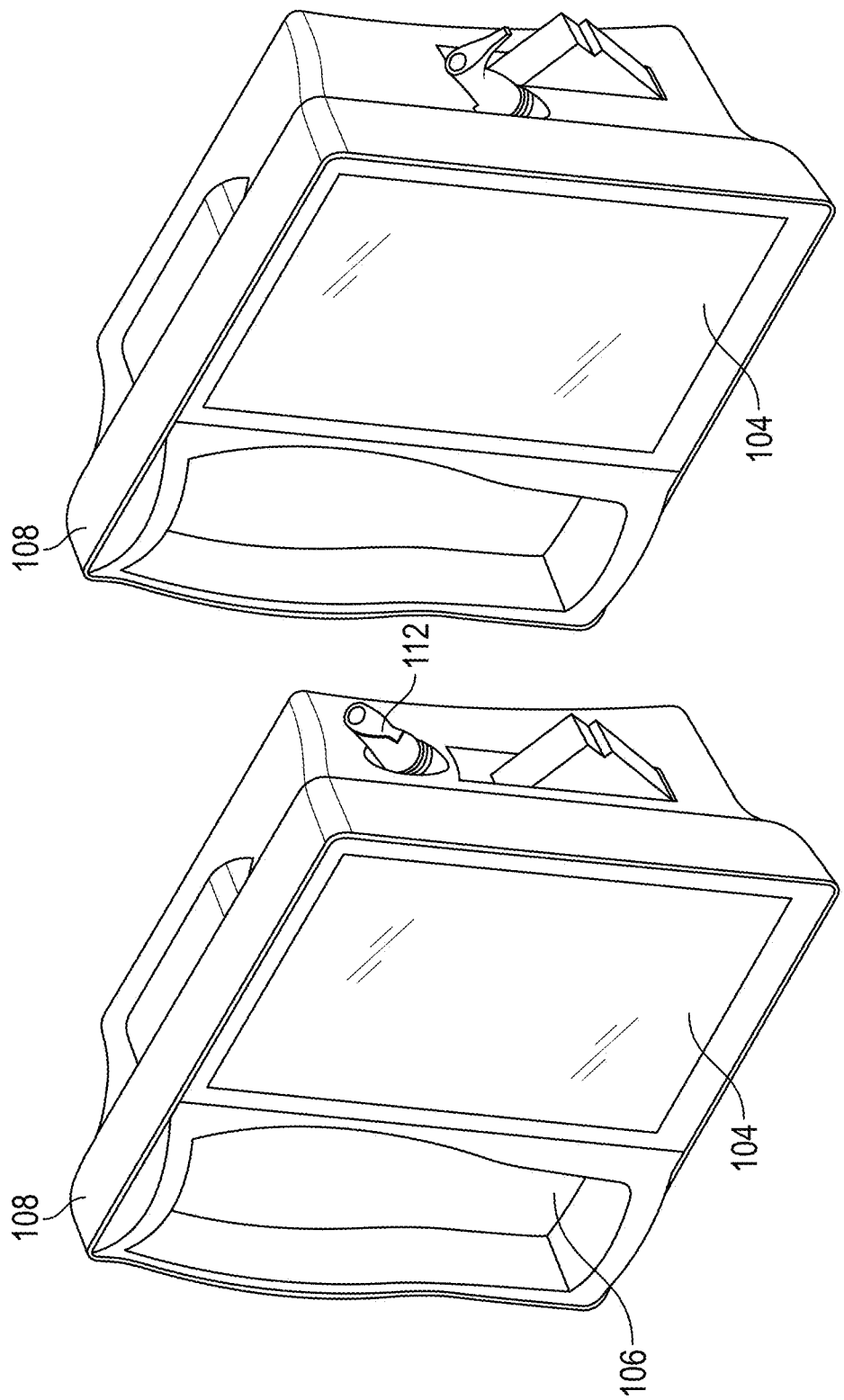

In an embodiment, the housing 108 may also include pockets or indentations to hold additional medical devices, such as, for example, a blood pressure monitor or temperature sensor 112, such as that shown in FIG. 1C.

The monitor 102 may communicate with a variety of noninvasive and/or minimally invasive devices such as optical sensors with light emission and detection circuitry, acoustic sensors, devices that measure blood parameters from a finger prick, cuffs, ventilators, and the like. The monitor 102 may include its own display 114 presenting its own display indicia 116. The display indicia may advantageously change based on a docking state of the monitor 102. When undocked, the display indicia may include parameter information and may alter orientation based on, for example, a gravity sensor or accelerometer.

In an embodiment, the docking station 106 of the hub 100 includes a mechanical latch 118, or mechanically releasable catch to ensure that movement of the hub 100 doesn't mechanically detach the monitor 102 in a manner that could damage the same.

Although disclosed with reference to particular portable patient monitors 102, an artisan will recognize from the disclosure herein a large number and wide variety of medical devices that may advantageously dock with the hub 100. Moreover, the docking station 106 may advantageously electrically and not mechanically connect with the monitor 102, and/or wirelessly communicate with the same.

Figure 2:
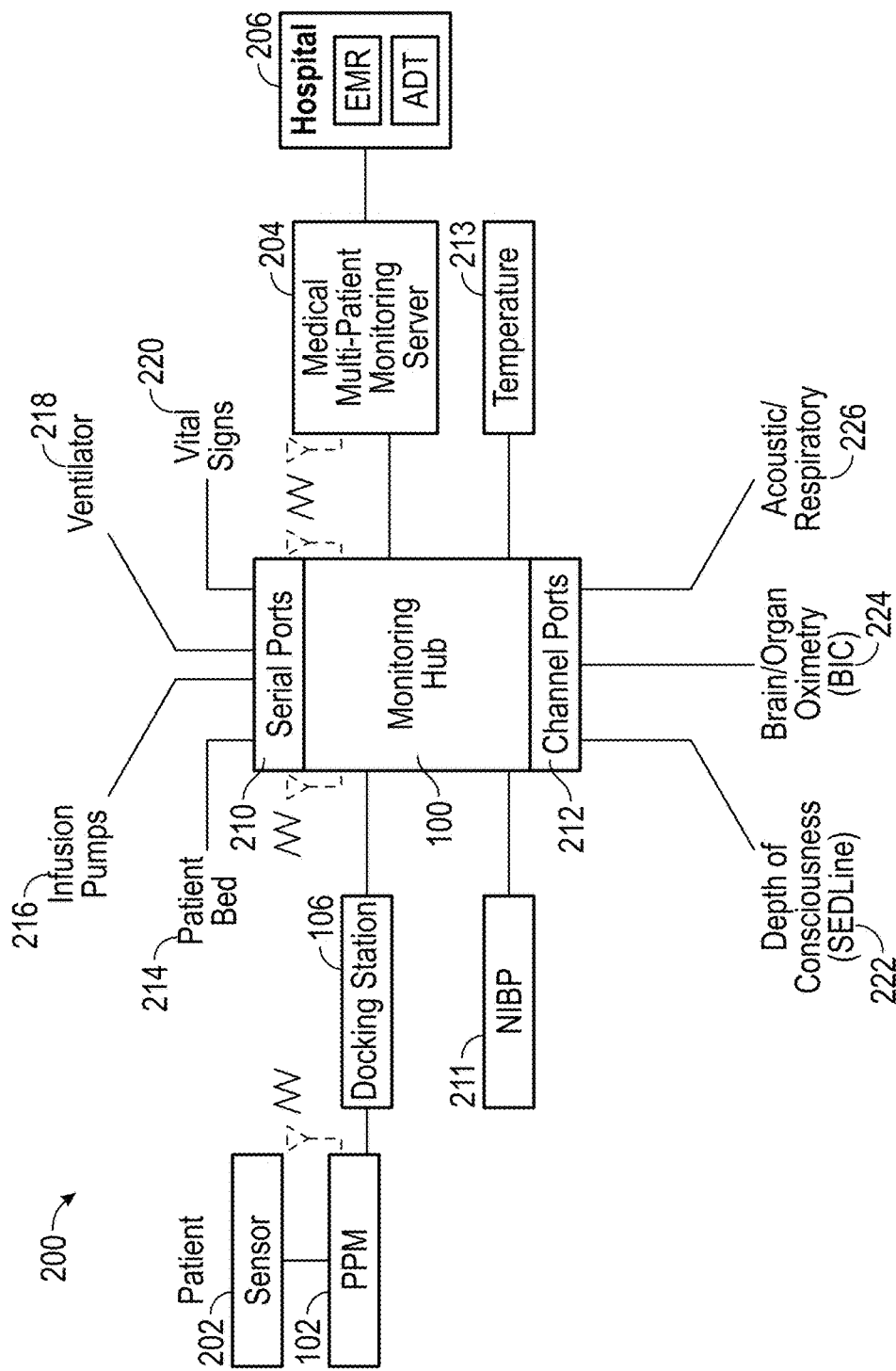
FIG. 2 illustrates a simplified block diagram of an exemplary monitoring environment including the hub of FIG. 1, according to an embodiment of the disclosure.

FIG. 2 illustrates a simplified block diagram of an exemplary monitoring environment 200 including the hub 100 of FIG. 1, according to an embodiment of the disclosure. As shown in FIG. 2, the environment may include the portable patient monitor 102 communicating with one or more patient sensors 202, such as, for example, oximetry optical sensors, acoustic sensors, blood pressure sensors, respiration sensors or the like. In an embodiment, additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

As disclosed, the portable patient monitor 102 communicates with the hub 100, in an embodiment, through the docking station 106 when docked and, in an embodiment, wirelessly when undocked, however, such undocked communication is not required. The hub 100 communicates with one or more multi-patient monitoring servers 204 or server systems, such as, for example, those disclosed with in U.S. Pat. Pub. Nos. 2011/0105854, 2011/0169644, and 2007/0180140. In general, the server 204 communicates with caregiver backend systems 206 such as EMR and/or ADT systems. The server 204 may advantageously obtain through push, pull or combination technologies patient information entered at patient admission, such as demographical information, billing information, and the like. The hub 100 accesses this information to seamlessly associate the monitored patient with the caregiver backend systems 206. Communication between the server 204 and the monitoring hub 100 may be any recognizable to an artisan from the disclosure herein, including wireless, wired, over mobile or other computing networks, or the like.

FIG. 2 also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from SEDLine, brain or other organ oximeter devices 224, noninvasive blood pressure or acoustic devices 226, or the like. In an embodiment, channel device may include board-in-cable ("BIC") solutions where the processing algorithms and the signal processing devices that accomplish those algorithms are mounted to a board housed in a cable or cable connector, which in some embodiments has no additional display technologies. The BIC solution outputs its measured parameter data to the channel port 212 to be displayed on the display 104 of hub 100. In an embodiment, the hub 100 may advantageously be entirely or partially formed as a BIC solution that communicates with other systems, such as, for example, tablets, smartphones, or other computing systems.

Although disclosed with reference to a single docking station 106, the environment 200 may include stacked docking stations where a subsequent docking station mechanically and electrically docks to a first docking station to change the form factor for a different portable patent monitor as discussed with reference to FIG. 5. Such stacking may include more than 2 docking stations, may reduce or increase the form fact for mechanical compliance with mating mechanical structures on a portable device.

Figure 3:
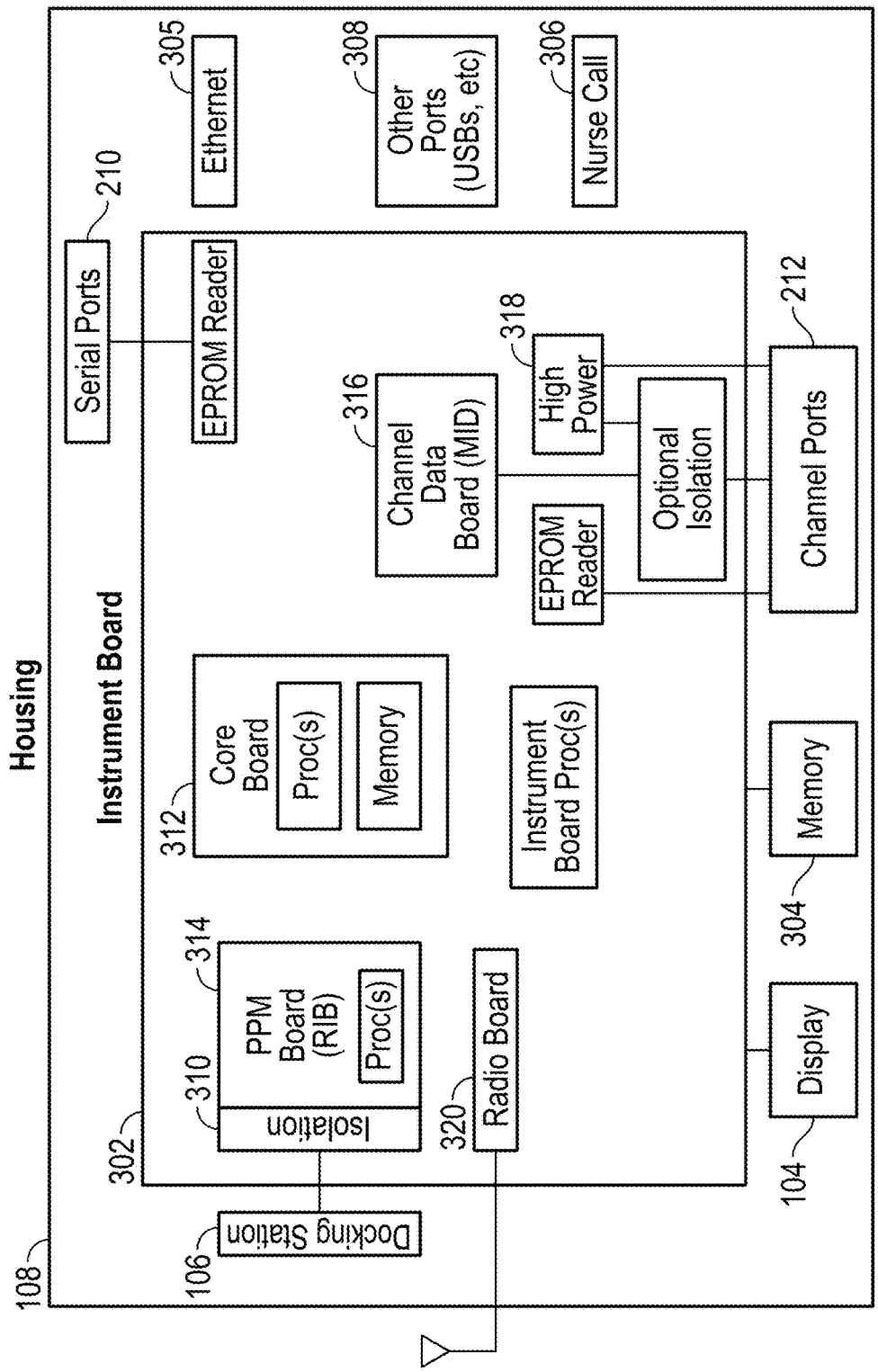
FIG. 3 illustrates a simplified exemplary hardware block diagram of the hub of FIG. 1, according to an embodiment of the disclosure.

FIG. 3 illustrates a simplified exemplary hardware block diagram of the hub 100 of FIG. 1, according to an embodiment of the disclosure. As shown in FIG. 3, the housing 108 of the hub 100 positions and/or encompasses an instrument board 302, the display 104, memory 304, and the various communication connections, including the serial ports 210, the channel ports 212, Ethernet ports 305, nurse call port 306, other communication ports 308 including standard USB or the like, and the docking station interface 310. The instrument board 302 comprises one or more substrates including communication interconnects, wiring, ports and the like to enable the communications and functions described herein, including inter-board communications. A core board 312 includes the main parameter, signal, and other processor(s) and memory, a portable monitor board ("RIB") 314 includes patient electrical isolation for the monitor 102 and one or more processors, a channel board ("MID") 316 controls the communication with the channel ports 212 including optional patient electrical isolation and power supply 318, and a radio board 320 includes components configured for wireless communications. Additionally, the instrument board 302 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 302 may comprise a large number of electronic components organized in a large number of ways. Using different boards such as those disclosed above advantageously provides organization and compartmentalization to the complex system.

Embodiments of Touch Screen Controls Including Certain Gestures

Figure 4:
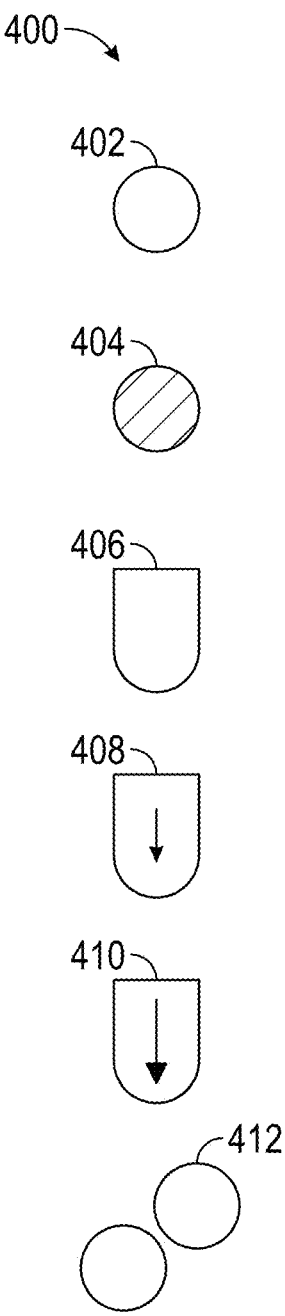
FIG. 4 is a finger control gesture legend for a touchscreen interface according to an embodiment of the disclosure.

FIG. 4 illustrates a legend of finger control gestures 400 for use with a touchscreen display 104 according to an embodiment. The finger control gestures 400 include a touch 402, a touch and hold 404, a touch and move 406, a flick 408, a drag and drop 410, and a pinch 412. A touch 402 is a finger control gesture that executes the desired action once the user's finger is released from the screen. A touch and hold 404 is a finger control gesture that executes the desired action once the user has held his or her finger on the screen continuously for a predetermined duration (e.g., a few seconds), received a "hold completion" notification, and has released his or her finger from the screen. A touch and move 406 is a finger control gesture that manipulates and/or translates objects across the display 104 in the desired and permitted direction to a deliberate stopping point. To execute a touch and move finger control gesture 406, the user touches an object, moves the object (left, right, up, down, diagonally, etc.), and releases the object. A flick 408 is a finger control gesture comprising contact of an object on the display 104 in conjunction with a quick finger movement in a particular direction, typically along a single vector. To execute a flick 408 finger control gesture the user touches an object on the display 104, moves the object (typically, but not necessarily in a single direction) and releases the finger from the display 104 quickly, in a manner such that the contact point has a velocity throughout its path of motion. A drag and drop 410 is a finger control gesture by which the user moves an object to another location or to another object (e.g., a folder) and positions it there by releasing it. To execute a drag and drop 410 finger control gesture, the user touches, holds, drags and drops the object. A pinch 412 is a finger control gesture that expands or contracts the field of view on the display 104. To execute a pinch 412 finger control gesture, the user touches the display 104 at two touch points using two fingers, for example, the thumb and index finger of a user's hand. Moving the touch points apart from each other zooms in on the field of view, enlarging it, while moving the touch points together zooms out on the field of view, contracting it.

In an embodiment the user interface includes multiple controls. For example, a toggle control enables a user to slide a knob to switch between toggle states. The toggle control also enables the user to press left or right of the toggle to quickly move the toggle left or right. If the toggle control is labeled, the user can press the label to quickly move the knob left or right.

The following paragraphs include a description of additional touch screen controls that can be used with the system of the present disclosure. The system can include any combination of the following controls and the present disclosure is not intended to be limited by the following descriptions of various controls.

In some embodiments, a spinner control enables the user to press a center (focused) tile to expand a spinner when the spinner is closed and to collapse a spinner when the spinner is opened. The spinner control enables the user to swipe up or down which, when the spinner is open, scrolls through spinner tiles. The spinner control enables the user to press an unfocused tile which then scrolls the tile into a center, focused position. And the spinner control enables the user to collapse an open spinner by pressing anywhere outside the spinner.

A slider control enables the user to move a knob by sliding the knob. The slider control also enables the user to quickly move the knob to a specific position by pressing anywhere along the slider path.

A slider spinner control combines the control capabilities of the spinner control and the slider control.

A button control enables a user to perform an action, as defined by the button description, by pressing the button.

An icon menu control enables the user to open a specified menu by pressing a tile. The icon menu control enables the user to scroll icons left or right by swiping left or right anywhere on the display. The icon menu control enables the user to quickly center a tile corresponding to an indicator icon by pressing an indicator button.

A window control enables the user to open a parameter or measurement window when no parameter or measurement alarm is present, by pressing the parameter or measurement. The window control enables the user to silence a parameter or measurement alarm when a parameter or measurement alarm is present, by pressing the parameter or measurement. The window control enables a parameter or measurement to be moved to a different location on the display 104 by using a drag and drop 410 finger control gesture.

A well control enables the user to open a parameter or measurement menu when no parameter or measurement alarm is present, by pressing the parameter or measurement. The well control enables the user to silence a parameter or measurement alarm when a parameter or measurement alarm is present, by pressing the parameter or measurement.

A live waveform control enables the user to separate waveforms by swiping down. The live waveform control enables the user to combine waveforms by swiping up.

A trend line control enables the user to zoom in by pinching in, zoom out by pinching out, change a time range by panning, and open a parameter or measurement trend menu by pressing the y-axis.

An alarm silence icon control enables the user to silence all alarms by pressing the alarm silence icon.

An audio pause icon control enables the user to pause audio for a predetermined period of time, by pressing the audio pause icon.

Other status bar icon controls enable the user to open the relevant menu, by pressing the relevant status bar icon.

A back arrow control enables the user to exit a menu or abandon any changes made, by pressing a back arrow icon.

A confirm-or-cancel control enables the user to confirm changes to settings by pressing an OK button. The confirm-or-cancel control enables the user to cancel changes to settings by pressing a cancel button.

A home control enables the user to navigate to the main screen at any time by pressing a home button.

Embodiments of Configurable Replay Display

Figure 5:
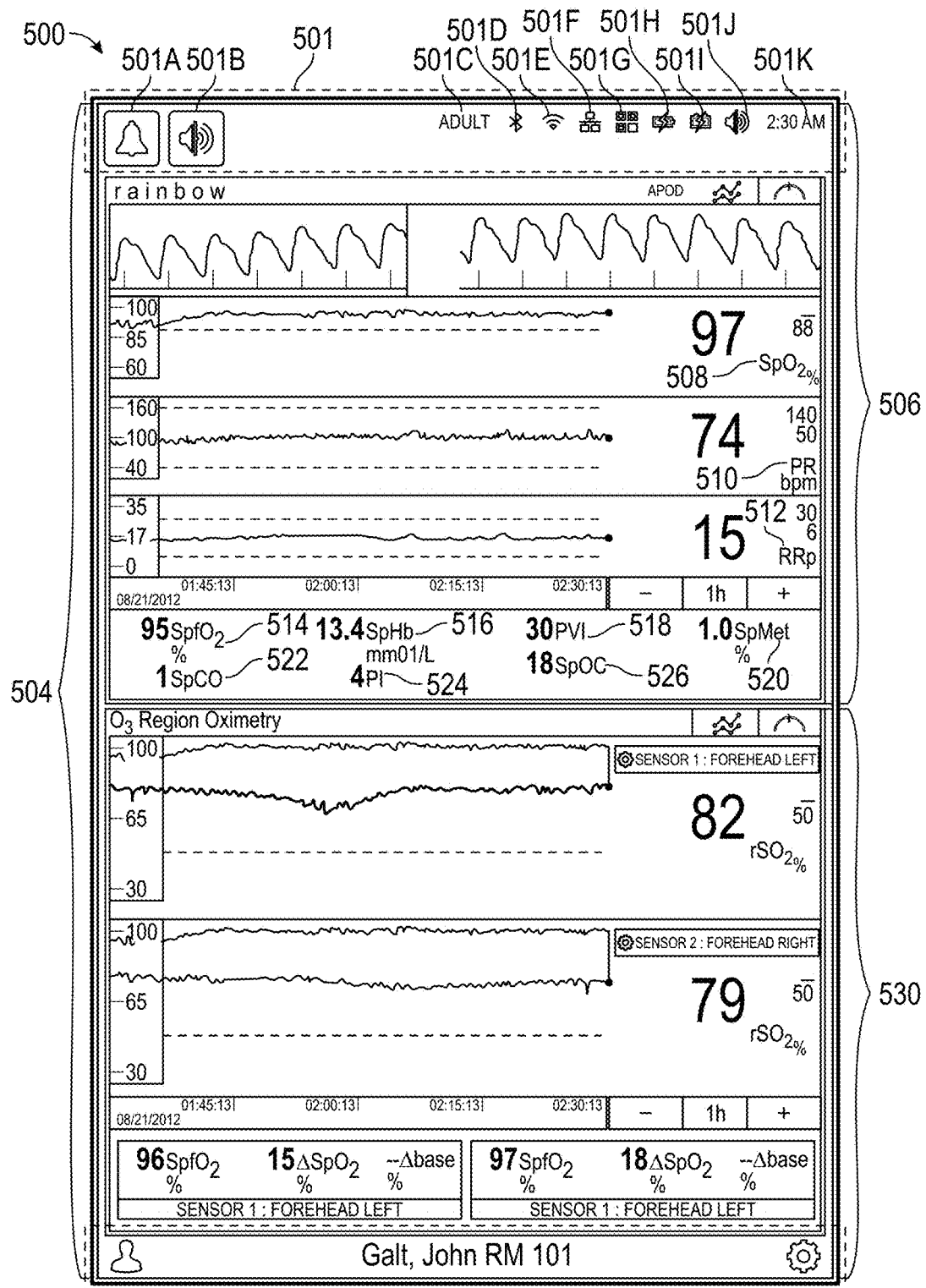
FIG. 5 is an illustration of a display view according to an embodiment of the disclosure.

FIG. 5 illustrates an embodiment of a user interface 500 displayed on the display 104 of the hub 100. In an embodiment the display 104 comprises a color, modular, touchscreen integral to the hub 100. Positioned horizontally along the top of the display 104 is a top status line 501 that displays system status as well as that provides shortcuts to menu items or actions. In an embodiment the icons presented on the top status line 501 include alarm silence 501A, audio pause 501B, profiles 501C, Bluetooth 501D, Wi-Fi 501E, Ethernet 501F, connectivity gateway 501G, portable patient monitor battery status 501H, monitoring hub battery status 501I, sounds 501J, and current time 501K.

The alarm silence icon 501A displays alarm status and mutes all audible alarms for monitoring devices connected to the hub 100. The audio pause icon 501B displays audio pause status and temporarily silences an alarm event. The profiles icon 501C provides access to a profiles screen; the example shown illustrates that the profile is set to "Adult" for an adult patient. The Bluetooth icon 501D provides access to a Bluetooth screen. If this icon is visible on the status line 501, then Bluetooth connectivity has been enabled. The Wi-Fi icon 501E provides access to a Wi-Fi screen. If this icon is visible on the status line 501, then Wi-Fi connectivity has been enabled. The icon itself also indicates the strength of the wireless signal. The Ethernet icon 501F provides access to an Ethernet screen. If this icon is visible on the status line 501, then Ethernet connectivity has been enabled.

The connectivity gateway icon 501G provides access to a connectivity gateway screen. The example illustrated indicates that standalone devices are connected to three of the available four ports. The color of the icon matches the status colors of the connected standalone devices. The portable patient monitor battery status icon 501H displays the charging status of the portable patient monitor 102 and provides access to a portable patient monitor battery screen. The example illustrates that the battery is currently charging. The monitoring hub battery status icon 501I displays the charging status of the monitoring hub 100 and provides access to a monitoring hub battery screen. The example illustrates that the battery is currently charging. The sounds icon 501J provides access to a sounds screen to adjust alarm and pulse tone volume. In an embodiment the sounds icon 501J does not indicate the actual volume level of the alarm and the pulse tone. The current time icon 501K displays the current time and provides access to a localization screen which contains settings related to local time, language and geography.

Positioned horizontally along the bottom of the display 104 is a bottom status line 502 that displays additional icons and information including a main menu icon, a gender icon, and a patient identifier that includes patient-specific information, such as, for example, the patient's name and room location. Although the disclosed embodiment employs status lines 501, 502 oriented horizontally along the top and bottom of the display 104, one skilled in the art would readily appreciate that information of the type presented in the top status line 501 and in the bottom status line 502 may be presented in numerous different formats, combinations and configurations, including without limitation, one or more status bars positioned vertically on the display 104. Moreover a skilled artisan will appreciate that other useful information may be displayed in status bars 501, 502.

In an embodiment the user interface can create a window for every monitoring device connected to the hub 100. Parameters or measurements can be expanded within a window to customize views. A central portion 504 of the display 104 presents patient measurement data, in this example, in two windows 506, 530. Illustratively, by way of non-limiting example, an upper window 506 presents patient data measured by an a noninvasive monitoring platform, such as the Rainbow® Pulse CO-Oximetry™ monitoring platform by Masimo Corporation of Irvine, Calif., which enables the assessment of multiple blood constituents and physiologic parameters including oxygen saturation ($SpO_2$) 508, pulse rate (PR) 510, respiration rate (RRp) 512, fractional arterial oxygen saturation ($SpfO_2$) 514, total hemoglobin (SpHb) 516, plethysmograph variability index (PVI) 518, methemoglobin (SpMet) 520, carboxyhemoglobin (SpCO) 522, perfusion index (PI) 524, oxygen content (SpOC) 526, or others. In the illustrated example, the lower window 530 of the display 104 presents patient data measured by a regional oximetry platform, such as the $O_3$™ regional oximetry module by Masimo Corporation of Irvine, Calif., which allows the continuous assessment of tissue oxygenation beneath one or more sensors placed on the patient's skin to help clinicians detect regional hypoxemia.

Advantageously, the display 104 is configurable to permit the user to adjust the manner by which the physiologic parameters are presented on the display 104. In particular, physiologic measurements of greater interest or importance to the clinician may be displayed in larger format and may also be displayed in both numerical and graphical formats to convey the current measurement as well as the historical trend of measurements for a period of time, such as, for example, the preceding hour. In an embodiment the oxygen saturation 508, pulse rate 510, and respiration rate 512 measurements are displayed in such a manner, taking up a larger portion of the upper portion 506 of the display 104, while the fractional arterial oxygen saturation 514, total hemoglobin 516, plethysmograph variability index 518, methemoglobin 520, carboxyhemoglobin 522, perfusion index 524, and oxygen content 526 measurements are displayed as numbers, taking up a smaller portion of the upper portion 506 of the display 104.

In an embodiment the presentation of measurement information may be adjusted easily by using the finger control gestures 400. For example, the touch and move 406 finger control gesture may be used to move an object on the display 104 representing a measurement from one location of the display 104 to another location of the display 104. Advantageously, when the object is moved, the display 104 automatically scales its presentation of information based upon the parameters that are active. For example, fewer parameters result in the presentation of larger digits, trend lines, and waveform cycles. In an embodiment the location to which an object is moved determines, at least in part, the manner by which that object will be presented on the display 104.

Attention is now directed to a plurality of analysis presentation views that may be presented on the disclosed monitoring hub 100. Advantageously, the disclosed monitoring hub 100 provides many analytical formats by which measured physiological parameters, as well as other data, can be displayed to the user. Size, format, color, and location on the display, among other things, can be easily set and modified by the clinician-user to readily customize the manner by which monitored physiological parameter data, as well as information derived therefrom, can be displayed.

Figure 6A:
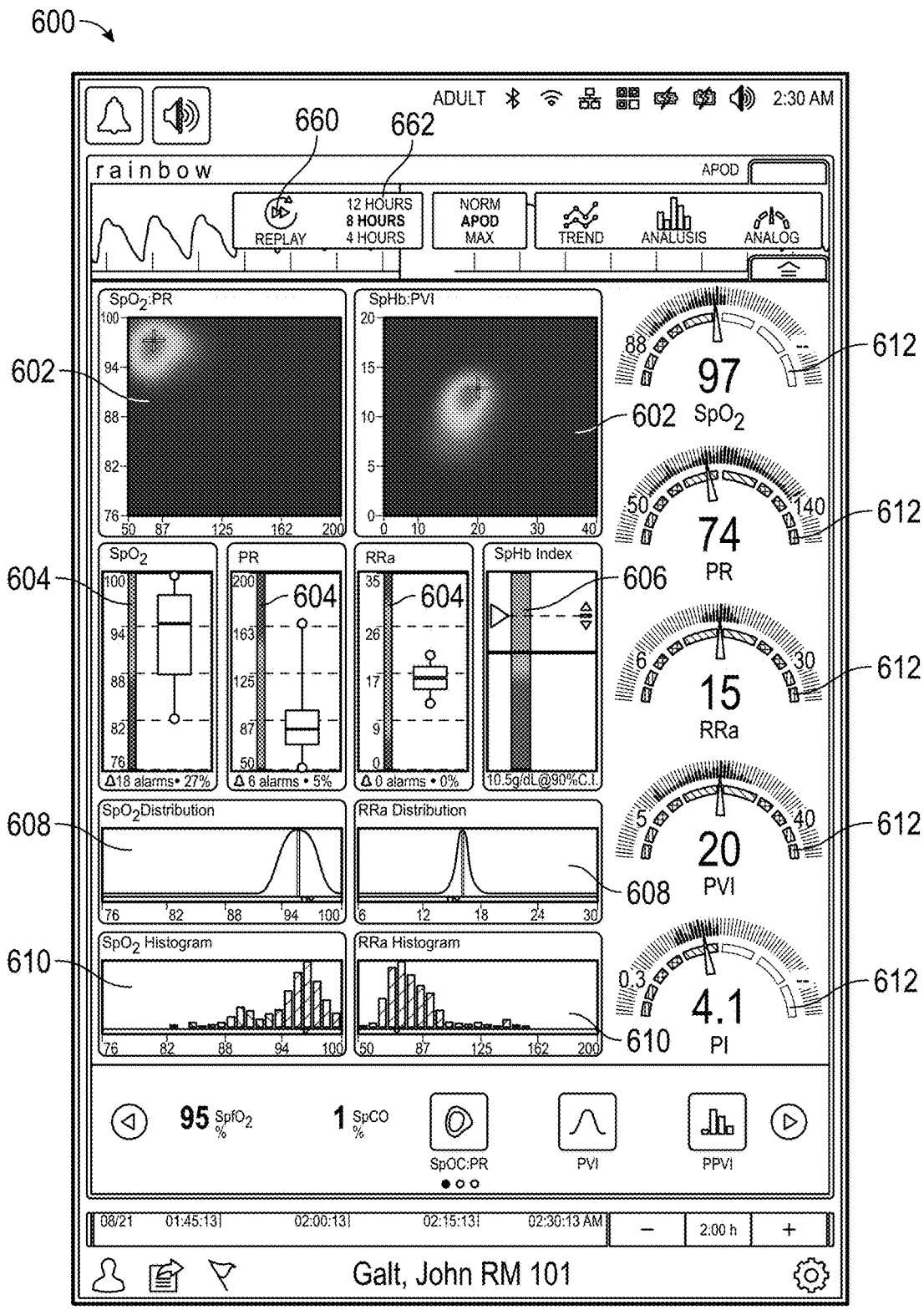
FIG. 6A illustrates an exemplary display screen showing various analytical presentation views for presenting received and processed data according to an embodiment of the disclosure.

FIG. 6A is an illustration of an exemplary display screen 600 showing various formats of analytical presentation views for illustrating received physiological parameter data, according to an embodiment of the disclosure. The exemplary display screen 600 includes heat map analytical presentation views 602, box-and-whisker analytical presentation views 604, an index analytical presentation view 606, distribution analytical presentation views 608, histogram analytical presentation views 610, and gauge-histogram analytical presentation views 612. The positions of each analytical presentation view may be adjusted and the format of each analytical presentation view may be substituted with other formats, advantageously resulting in a high degree of customization for the user. For example, the gauge-histogram presentation views 612 are situated vertically in a right side panel portion of the screen 600, but may instead be situated in any formation and in any position on the screen 600.

Heat Maps

A heat map 602 analytical presentation view provides a two-dimensional graphical representation of a relationship between two measured parameters over a specified period of time, using color to identify areas in the graph where the data is concentrated. For example, as illustrated in FIG. 6B, the heat map 602 presents the relationship between measured oxygen saturation (SpO2) and pulse rate (PR) at specific points in time. Illustratively, by way of non-limiting example, an area on the graph corresponding to the highest concentration of correlated values between measured oxygen saturation and pulse rate is colored in a first color (e.g., red). FIG. 6B shows the heat map centered around an SpO2 value of about 98% and a PR value of about 61 bpm. Moreover, FIG. 6B shows that as the concentration of correlated measurements decreases, the colors on the heat map change (e.g., from red to orange, then to yellow, then to green, and finally to blue) indicating progressively lower concentrations of correlated values between the two measured parameters.

Heat maps 602 advantageously provide a trend of multiple monitored values or physiological parameters at a mere glimpse. For example, FIG. 6B shows a caregiver that while the PR for the patient may be a little low, depending on age, fitness, activity level during monitoring, or the like, the patient was almost if not entirely fully saturated with oxygen. Thus, because the body appears to be oxygenated, additional PR may not be needed during the time period presented. Accordingly and advantageously, the heat map 602 delivers a visual summary of the data that enables the user to intuitively understand and analyze complex relationships between data sets.

Box-and-Whisker Plots

In descriptive statistics, a box plot or boxplot is a convenient way of graphically depicting groups of numerical data through their quartiles. Box plots may also have lines extending vertically from the boxes (whiskers) indicating variability outside the upper and lower quartiles, these are often called box-and-whisker plots or diagrams. The spacings between the different parts of the box indicate the degree of dispersion (spread) and skewness in the data, and show outliers.

As shown in FIG. 6C, a box-and-whisker plot analytical presentation view 604 visually presents the range of measurements received over a specified or pre-determined period of time, and the boundaries of the quartiles in which the data lies. Advantageously, the box-and-whisker view 604 readily presents to the user the degree of spread, or dispersion, of the measured data, as well as the skewness in the data, including outlier measurements. The whiskers 620 and 622 identify the low end and high end, respectively, of the range of measurements displayed.

By way of illustrative example, as depicted in FIG. 6C, the range of measured SpO2 data for a given patient may extend from 82% to 100%. An artisan will recognize other patient's may have many other ranges. The box 624 identifies the median line 626 of the measured SpO2 parameter data. Thus, half of the measured SpO2 data represented by the view 604 falls above the median line 626 and half of the measured SpO2 data falls below the median. The lower edge 628 and the upper edge 630 of the box 624 identify the medians of the lower and upper half of the measured SpO2 data, respectively. Thus, as illustrated in FIG. 6C, a first quartile of measured SpO2 data lies between the end point of the bottom whisker 620 and the bottom edge 628 of the box 624; a second quartile of measured SpO2 data lies between the bottom edge 628 of the box 624 and the median line 626; a third quartile of measured SpO2 data lies between the median line 626 and the top edge 630 of the box 624; and a fourth quartile of measured SpO2 data lies between the top edge 630 of the box 624 and the end point of the top whisker 622.

Again, box-and-whisper plots 604 advantageously provide a trend of a monitored value or physiological parameter at a mere glimpse. For example, FIG. 6C shows a caregiver that while SpO2 varied somewhat, at least half the time it was above about 94% and a quarter of the monitored window SpO2 was between about 94% and about 98%. While about half of the time, SpO2 was lower than perhaps desired.

Index Views

An index analytical presentation view 606, such as the continuous, noninvasive measurement of arterial hemoglobin concentration, which may also be referred to as a "total hemoglobin" (SpHb) index 606, exemplarily illustrated in FIG. 6D, presents a current measured state of a physiological parameter (SpHb, in this example) relative to ranges identified as acceptable, cautionary, and emergent. As illustrated in FIG. 6D, an indicator 632 shows a current measured parameter level relative to a vertical bar 634. The vertical bar 634 is shaded in different colors, such as, for example, green, yellow and red. The colors can be used to identify different regions or zones corresponding to, for example, acceptable, cautionary, and emergent values of the measured parameter. A threshold line 636 can be set to visually identify one zone from another. Illustratively, by way of non-limiting example, the threshold line 636 can identify the boundary between the range of acceptable values and the range of cautionary values of the measured parameter. In an embodiment, the user can set the ranges and boundary conditions for such ranges. In other embodiments, the ranges and boundary conditions for a given physiological parameter are set to default values corresponding to generally clinically accepted values for such ranges. The units of the measured parameter can be presented in a well 638 at the bottom of the index analytical presentation view 606. For example, as illustrated in FIG. 6D, the units of the physiological parameter being measured (total hemoglobin, SpHb) are in grams per deciliter (g/dL) at a confidence interval (C.I.) of ninety percent. Advantageously, the index analytical display provides to the user an easily-interpreted presentation of the measured physiological parameter.

Distribution Views

Figure 6E:
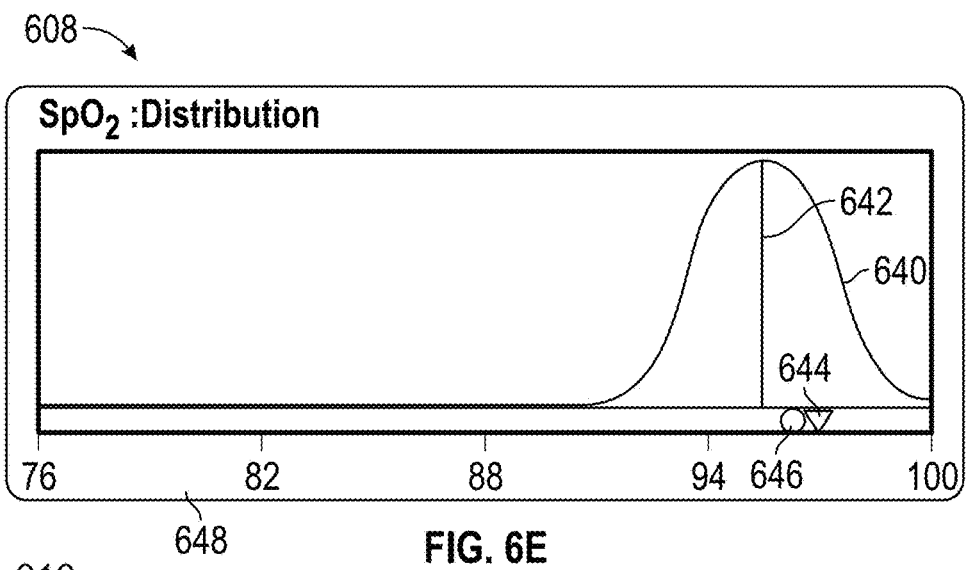
FIG. 6E illustrates a distribution analytical presentation view according to an embodiment of the disclosure.

A distribution analytical presentation view 608, such as the SpO2 distribution display 608 illustrated in FIG. 6E, presents a statistical distribution of a set of physiological parameter measurements over a specified or pre-defined period of time. The distribution analytical presentation view 608 provides the user a visual representation of the range of physiological parameter measurements collected as well as a statistical distribution associated with such measurements. Illustratively, by way of non-limiting example, the distribution analytical presentation view 608 shown in FIG. 6E presents a distribution 640 of the oxygen saturation (SpO2) parameter measurements over a period of time. In the example depicted in FIG. 6E, the distribution 640 is substantially normal (or Gaussian) with its mean (or expected value) 642 illustrated as well. A current measured value indicator 644 informs the user of the present state of the patient, and a standard deviation indicator 646 indicates the degree to which the measured data varies or disperses over the range of values. A well 648 toward the bottom of the distribution analytical display 608 provides numerical units of the measured physiological parameter, such as percentage for the oxygen saturation measurement.

Histogram Views

Figure 6F:
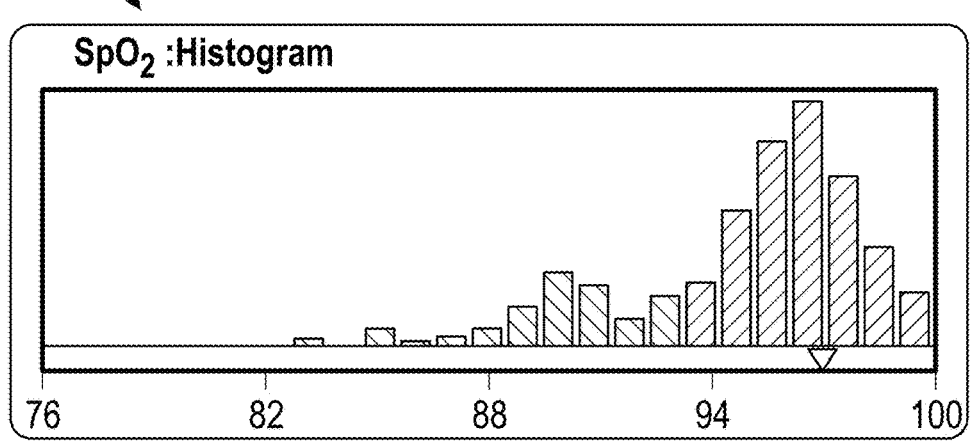
FIG. 6F illustrates a histogram analytical presentation view according to an embodiment of the disclosure.

A histogram analytical presentation view 610, as illustrated in FIG. 6F, provides another graphical representation of a collection of measured physiological parameter data. A histogram represents an estimate of the statistical (or probability) distribution of a continuous variable, such as a continuously measured physiological parameter. Thus, rather than providing a statistical distribution (i.e., a probabilistic model) that best fits or corresponds to the measured data, the histogram reflects the actual measured data collected. To form a histogram, the entire range of values to be measured is divided into a series of often equally-spaced, often consecutive, often non-overlapping intervals, referred to as "bins." Each physiological parameter measurement value is then allocated to one of the bins. A bar is drawn for each bin, where the height of the bar corresponds to the number of discrete physiological parameter measurements that fall within that bin's particular range. In an embodiment, the width of each bar is constant, corresponding to the ranges of the equally-spaced intervals. The histogram may also be normalized to display the relative frequency or proportion of measurements that fall into each of the several bins. Advantageously, the histogram analytical presentation view 610 provides the user a visual representation of the actual frequencies of the observed physiological parameter measurements in certain ranges of values.

Analog Gages Including Histogram Views

Figure 6G:
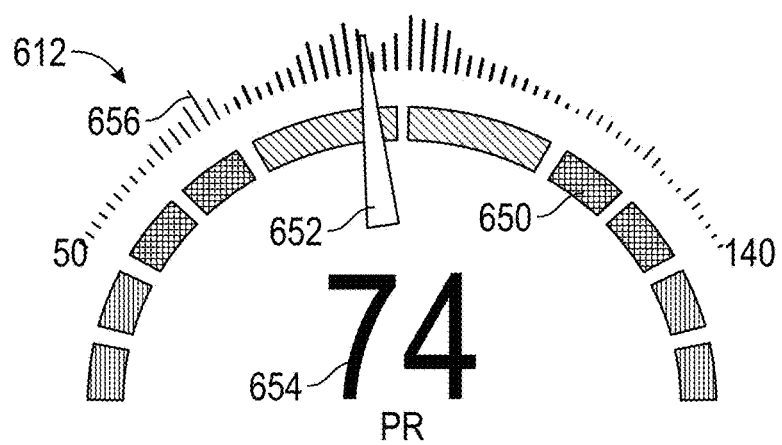
FIG. 6G illustrates a gauge-histogram analytical presentation view according to an embodiment of the disclosure.

A gauge-histogram analytical presentation view 612, as illustrated in FIG. 6G, provides a combination of analog, digital and histogram display indicia in one presentational format view. Advantageously, the gauge-histogram analytical presentation view 612 provides to the user a substantial amount of information related to the measured physiological parameter in an intuitive and visually accessible format. The gauge-histogram 612 includes an analog indicator forming, for example, a semi-circular arc 650. Portions of the arc 650 can be differentiated by use of various colors or shading to indicate different regions of measured parameter values, such as, for example, acceptable, cautionary and emergent regions of the gauge. Illustratively, by way of non-limiting example, the acceptable range of values can be colored green, and can be located generally centrally within the arc 650, while cautionary ranges of values can be colored yellow and located beyond the acceptable range of values, and emergent ranges of values can be colored red and located beyond the cautionary value ranges toward the two ends of the arc 650. Of course, one skilled in the art will appreciate that many other colors and range formats may be used without departing from the scope of the present disclosure.

The gauge-histogram analytical presentation view 612 can include a dial marker 652 that moves about the arc 650 reflecting the current measured level of the monitored physiological parameter. Illustratively, by way of non-limiting example, as the measured physiological parameter level increases, the dial can move clockwise, and as the measured physiological parameter level decreases, the dial can move counter-clockwise, or vice versa. In this way, a user can quickly determine the patient's status by looking at the analog indicator. For example, if the dial marker 652 is in the center of the arc 650, the observer can be assured that the current physiological parameter measurement falls within the acceptable range. If the dial marker 652 is skewed too far to the left or right, the observer can quickly assess the severity of the physiological parameter level and take appropriate action. In other embodiments, acceptable parameter measurements can be indicated when the dial marker 652 is to the right or left, etc.

In some embodiments, the dial marker 652 can be implemented as a dot, a dash, an arrow, or the like, and the arc 650 can be implemented as a circle, a spiral, a pyramid, or any other shape, as desired. Furthermore, the entire arc 650 can be illuminated or only portions of the arc 650 can be illuminated, based for example, on the current physiological parameter being measured. Additionally, the arc 650 can turn colors or be highlighted based on the current measured physiological parameter level. For example, as the dial marker 652 approaches a threshold level, the arc 650 and/or the dial marker 652 can turn from green, to yellow, to red, shine brighter, flash, be enlarged, move to the center of the display, sound an alarm, or the like.

Different physiological parameters can have different thresholds indicating abnormal conditions. For example, some physiological parameters may have upper and lower threshold levels, while other physiological parameters may only have an upper threshold or a lower threshold level. Accordingly, each gauge-histogram analytical presentation view 612 can be adjusted based on the particular physiological parameter being monitored. Illustratively, by way of non-limiting example, an SpO2 gauge-histogram presentation view 612 can have a lower threshold, which when met, activates an alarm, while a respiration rate gauge-histogram presentation view 612 can have both a lower and an upper threshold, and when either threshold is met, an alarm can be activated. The thresholds for each physiological parameter can be based on typical, expected thresholds, or they can be set to user-specified threshold levels.

In certain embodiments, such as the embodiment illustrated in FIG. 6G, the gauge-histogram analytical presentation view 612 includes a digital indicator 654. The analog arc 650 and digital indicator 654 can be positioned in any number of formations relative to each other, such as side-by-side, above, below, transposed, etc. In the illustrated embodiment, the analog arc 650 is positioned above the digital indicator 654. As described above, the analog arc 650 and dial marker 652 may include colored warning sections, indicating a current position on the graph. The digital information designates quantitative information from the graph. In FIG. 6G, for example, the gauge-histogram analytical presentation view 612 displays pulse rate information. The arc 650 shows that from about 50 to about 140 beats per minute, the measured pulse rate physiological parameter is either in the acceptable range or beginning to enter the cautionary range, whereas in the regions outside those numbers, the arc 650 is colored to indicate an emergent or severe condition. Thus, as the dial marker 652 moves along the arc, 650, a caregiver can readily see where in the ranges of acceptable, cautionary, and emergent pulse rate values the current measurement falls. The digital indicator 654 provides a numerical representation of the current measured value of the physiological parameter being displayed. The digital indicator 654 may indicate an actual measured value or a normalized value, and it can also be used to quickly asses the severity of a patient's condition.

As illustrated in FIG. 6G, a histogram arc 656 is located above and surrounding the arc 650, having multiple radially-extending lines that correspond to histogram bins (as described above with respect to FIG. 6F) for the measured physiological parameter. The bins of the histogram arc 656 can be illuminated to reflect the distribution of measured parameter values in the manner described above with respect to the histogram analytical presentation view 610. In the embodiment illustrated in FIG. 6G, the bins are illuminated in colors corresponding to the ranges along the arc 650 in which they fall. Thus, the disclosed gauge-histogram analytical presentation view 612 provides analog and digital indicia of the current measured physiological parameter, correlated with range information indicative of the level of urgency required for the measured parameter, as well as a visual display of the actual distribution of the patient's parameter measurements over a period of time.

Advantageously, the hub 100 stores the measured data that it has presented on the display screen 600 over time. In certain embodiments, the data is stored in the memory 304 of the instrument board 302. In certain embodiments, the stored externally and accessed by the monitoring hub 100 via a network connection, such as, for example, an Ethernet connection. In still other embodiments, the data is stored in both on-board memory 304 and external storage devices.

Drag and Drop

Referring back to FIG. 6A, each of the foregoing display elements 6B, 6C, 6D, 6E, 6F and 6G can be dragged onto the screen and dropped to create a customized view to match a caregiver's preferences for a particular monitored patient. In an embodiment, a display element and its particular displayed parameters are shown as icons along a bottom horizontally scrollable menu. When a caregiver wishes to place, for example, a Perfusion Variability Index (PVI) distribution view on the screen, he or she could select the PVI distribution icon from the bottom well, scroll, and drag it to the screen to, for example, replace any existing display element. In another embodiment, a caregiver may select a display element and then select the parameter or parameters to be provided to the element.

Replay

FIG. 6A also shows the display screen 600 provides a replay feature, which permits the clinician to review a historical record of the patient data collected and processed by the monitor 100. A user may select a time frame 662 for a replay period. For example, a user may select between replaying a previous ten-minute period, a four-hour period, or an eight-hour period. Any amount of time may be a suitable replay period. In an embodiment, the screen 600 may provide a default time frame 662, for example eight hours. After a replay period is selected or a default period is determined, a user may select a replay icon 660 to begin replay.

In certain embodiments, the stored data may be replayed on different monitor hubs or on different displays (such as, for example, a display connected to a multi-patient monitoring server 204), to permit clinicians who are remote from the patient's care environment to access and review the monitored data.

During a replay period, stored data may be displayed on the screen 600 at different rates. For example, the replayed data can be displayed at the same rate of time in which the data was originally presented. Thus, replaying one hour of recorded data would take one hour to fully replay. Alternatively, the replayed data can be displayed in slow-motion (slower than real-time), or in a time-lapse (faster than real-time) formats. For example, to replay in slow-motion, the screen 600 may present each frame of data for a longer period of time than originally presented. Illustratively, by way of non-limiting example, slow-motion replay can be useful to review and analyze portions of the recorded physiological parameter data in which abrupt changes occur. Time-lapse replay permits the clinician to review a period of recorded data over a shorter period of time than the data was originally presented. In an embodiment, to replay in time-lapse mode, a screen 600 may accelerate a speed at which frames are displayed. In another embodiment, to replay in time-lapse mode, a screen 600 may display only a sampling of frames from a set of data. For example, a screen 600 may display every fifteenth frame so that data may be presented in a shorter time while still providing a useful illustration of the stored data. In an embodiment, the user can select the rate at which the time-lapse replay will progress. For example, by way of illustration, the user might choose to view one minute's worth of real-time data in one second or in ten seconds. This information may be particularly useful to a care provider who would like to quickly review a patient's physiological conditions from a previous time period when, for example, the care provider was not present to observe the data as it was originally presented.

Figure 7:
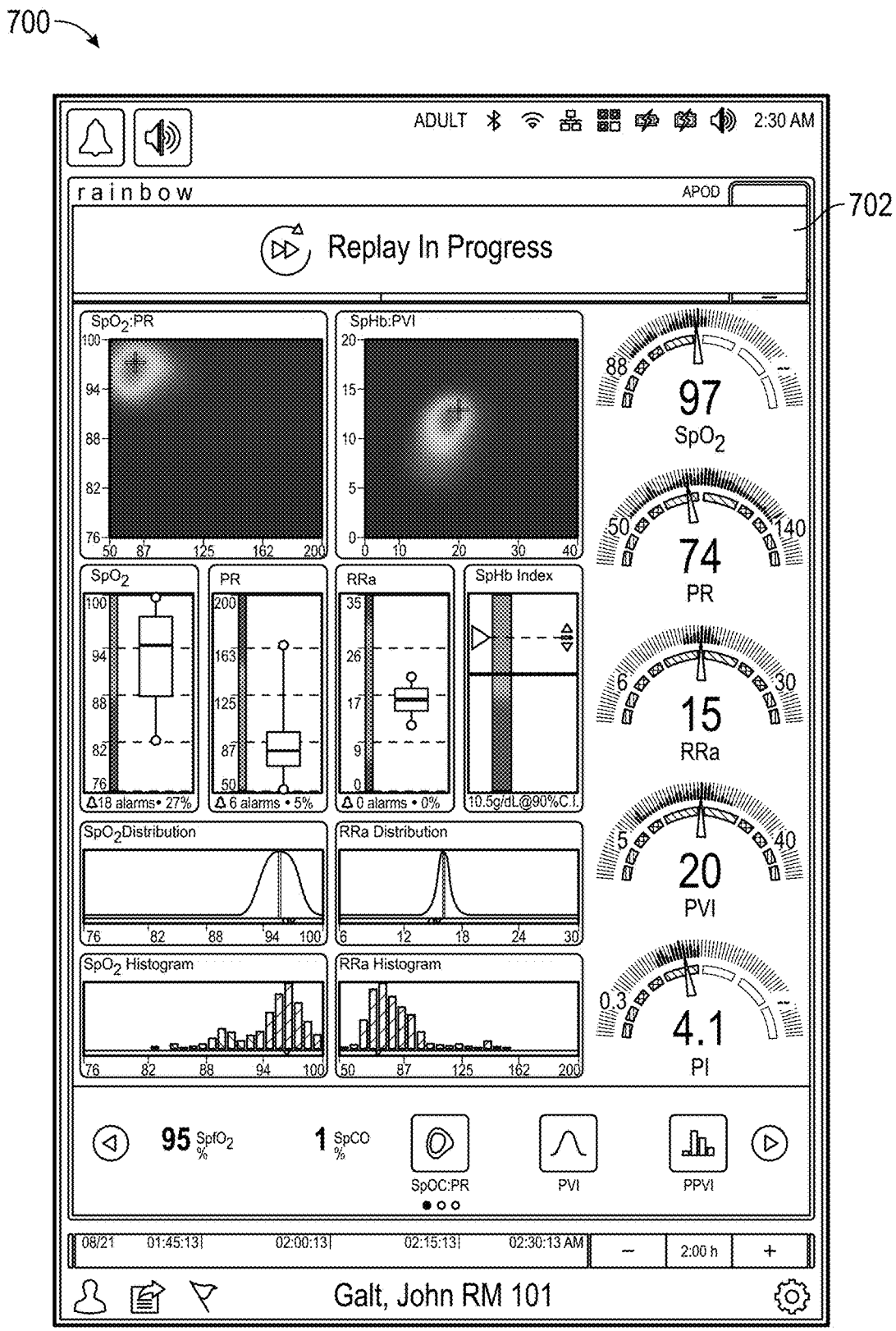
FIG. 7 illustrates an exemplary display screen showing a replay feature according to an embodiment of the disclosure.

In certain embodiments, multiple parameter displays presented on the screen 600 may synchronously replay stored data during a replay period, while other parameter displays may present live data. This allows the clinician to concurrently monitor the present condition of the patient and review (i.e., replay) past measurement data. Illustratively, by way of non-limiting example, a series of analytical displays in a center portion of the screen 600 may replay stored data, while a series of gauge-histogram analytical displays 612, located in a side panel, may present live data. In another embodiment, every feature on the screen 600 may replay stored data during a replay period. FIG. 7 illustrates such an example, and the display 700 provides a message 702 indicating that the displayed data is being replayed. In yet another embodiment, any single analytical display or combination of analytical displays on the screen 600 may present live data during a replay period. In some embodiments, individual analytical displays may have individual icons or indicators (not shown) associated with them to indicate whether the analytical presentation view is presenting live or stored and replayed data. In some embodiments, an individual display element may include both replayed and live data.

Figure 8:
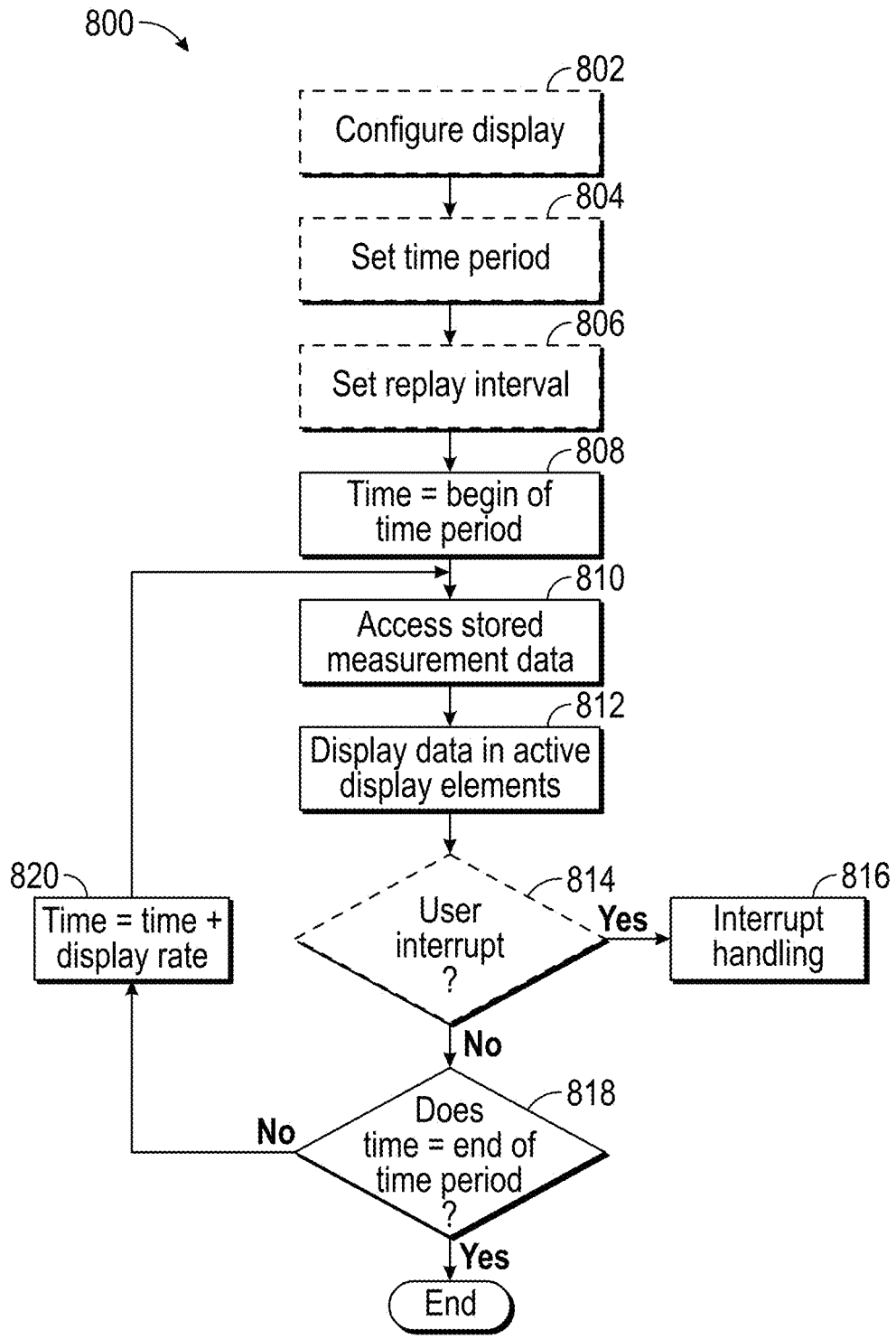
FIG. 8 is a flowchart illustrating a replay process according to an embodiment of the disclosure.

FIG. 8 is a flowchart illustrating a replay process 800 according to an embodiment of the present disclosure. At optional block 802, a user configures the display 600 with the display elements a caregiver desires for the monitored patient. The drag and drop functionality allows the user to straightforwardly drag the display elements to the portion of the screen desired. In an embodiment, a default screen layout could be implemented. Alternatively or additionally, the screen may be set to the most recent replay configuration, a replay configuration matched to a known user, known caregiver, or the patient, or some or all of the foregoing.

In optional block 804, the user sets a time period for replay. As discussed above, any amount of time may be a suitable time period. For example, a user may choose between a two-hour, four-hour, eight-hour, or ten-minute replay period. In an embodiment, a user may select a timeframe icon 662 to set the time period. In other embodiments, the user can scroll backward on a timeline (not shown) to select a starting point and ending point for the replay. In other embodiments, the user can input a start time and end time for the replay.

At optional block 806, the user may select a replay interval which defines the rate at which the replay displays. In certain embodiments, the replay interval includes real-time, slow-motion, and time-lapse intervals. Illustratively, a replay interval may be indicative of the number of frames of stored data which are displayed when selecting a time-lapse mode of replay. For example, a user may choose to have every fifteenth frame or every tenth frame of recorded data to be displayed in order to shorten the time required to replay stored data. In other embodiments, the user may be presented a timeline the width of the optionally selected time period and the user may pinch the timeline bigger or smaller to automatically adjust the interval.

At block 808, time is set to the start of the time period. At block 810, measurement data is accessed. In an embodiment, a processor accesses only the data used in the active display elements; in other embodiments, all the data associated with a particular time is accessed. In an embodiment, the processor synchronizes data to the display time even though such data may not be from the same measurement device. In other embodiments, synchronization data may be stored along with the original measurement data for use when accessed during the replay process 800.

At block 812, the data is displayed to the user through the configured display elements. At optional block 814, a user may interrupt replay to pause, speed up or slow down the replay, zoom in or out on a time period, switch to another time period, end replay, change display elements, or otherwise manipulate the data being replayed. In optional block 816, such interrupts are handled and appropriate action is taken, such as, for example, restarting replay with new configuration or time parameters.

At block 818, the process 800 determines if playback has reached the end of the selected playback time period. If so, the process 800 ends; if not, the display rate is added to the current display time and the process 800 returns to block 810 to access additional data.

Advantageously, process 800 allows a caregiver to straightforwardly monitor a wide variety of measurements and combinations of measurements for a particular time period. For example, the caregiver may see during replay a heat map 602 fluctuate in color and/or position, pulse or otherwise show how the body of the patient is oxygenated and what pulse rate it is using for such oxygenation. Likewise, box-and-whisker plots 604 may have portions that grow, shrink, and move in rhythm with, for example, the heat map 602. Distributions 608 may change and histograms along with their analog gages may provide indications of how the body is reacting over a course of pre-selected time.

As discussed above, a user may run a replay process by selecting a replay icon 660. Once the replay process is complete, a user may choose whether to repeat the process, at block 808. If the user chooses to repeat the process, the process 800 will again run at step 806. If the user chooses not to repeat the process, the process will end at block 810.

Thus, a patient monitoring hub that serves as the center of patient monitoring and treatment activities for a given patient is disclosed. Embodiments of the patient monitoring hub include a large visual display that dynamically provides information to a caregiver about a wide variety of physiological measurements or otherwise-determined parameters. Advantageously, the display can be customized by the clinician-user to present the desired physiological parameters (and other relevant information) in the formats and at the locations on the display that the clinician desires. Numerous analytical presentation views are provided to present the monitored physiological parameters (and other information) in visual formats that provide timely, clinically-relevant, and actionable information to the care provider. Additionally, the disclosed monitoring hub allows for replay of all or portions of the monitored data in a synchronized manner. The embodiments disclosed herein are presented by way of examples only and not to limit the scope of the claims that follow. One of ordinary skill in the art will appreciate from the disclosure herein that many variations and modifications can be realized without departing from the scope of the present disclosure.

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The term "plethysmograph" includes it ordinary broad meaning known in the art which includes data responsive to changes in volume within an organ or whole body (usually resulting from fluctuations in the amount of blood or air it contains).

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A medical monitor including a configurable replay display, said monitor configured to analyze and present indicia reflective of physiological parameters of a patient in real time and replayed for stored data, said parameters including oxygen saturation, the monitor comprising:
    a housing;
    said housing positioning at least one sensor port, said sensor port configured to receive a first signal responsive to light attenuated by tissue of a wearer of at least one noninvasive sensor;
    said housing positioning at least one communication port, said at least one communication port configured to receive other data responsive to physiology of said wearer from devices separate and different from said medical monitor;
    said housing positioning a touchscreen display;
    said housing enclosing a processing system including a plurality of processors, one or more of said plurality of processors configured to process said received first signal and determine first data indicative of a first physiological parameter, said first data including at least one waveform, measurement values of said first physiological parameter, and when applicable, visual alarms associated with said measurement values, wherein one or more of said plurality of processors is configured to receive said other data and timewise synchronize the first data with said other data, wherein said first data and said other data need not be determining measurement values at the same rate, wherein one or more of said plurality of processors are configured to process said first data or said other data or both, to create virtual channel data including non-measured parameter data resulting from processing said first data or said channel data or both;
    wherein said touchscreen display is responsive to one or more of said plurality of processors to present a configurable replay display view including a plurality of presentation views, said plurality of presentation views being user-selectable to include a heat map view and two or more of a box-and-whisper view, a distribution view, a histogram view, an index view, or a gage histogram view; and
    said housing enclosing a storage device configured to store said first data, said virtual channel data, and said other data for use during a replay process;
    wherein said touchscreen display is responsive to at least a plurality of finger control gestures made while in contact with said touchscreen display and within the configurable replay display view to replay past values of said stored first data, said virtual channel data, and when selected, said other data, formatted into said configurable replay display view including selected ones of said plurality of presentation views, said replay automatically formatting said past values according to axis alterations in response to said control gestures made within said configurable replay display view.

2. The monitor of claim 1, wherein the touchscreen display is responsive to said control gestures to present an entirety of said replayed first data, said virtual channel data, and when selected, said other data for a duration that is shorter than when said first data, said virtual channel data, and said other data was presented in real time.

3. The monitor of claim 1, wherein the touchscreen display is responsive to said control gestures to present an entirety of said replayed first data, said virtual channel data, and when selected, said other data for a duration that is longer than when said first data, said virtual channel data, and said other data was presented in real time.

4. The monitor of claim 1, wherein the touchscreen display is responsive to said control gestures to present said replayed first data, said virtual channel data, and when selected, said other data formatted for a duration that is equal to than when said first data, said virtual channel data, and said other data was presented in real time.

5. The monitor of claim 1, wherein said heat map view is further configured to present a relationship between said first physiological parameter and a second physiological parameter and to identify an area in said heat map view in which second data indicative of said second physiological parameter is concentrated.

6. The monitor of claim 5, wherein said heat map view is further configured to identify a first area in said heat map view associated with a first concentration of said second data and a second area in said heat map view associated with a second concentration of said second data, wherein said first area is presented in a first color and said second area is presented in a second color.

7. The monitor of claim 5, wherein said first physiological parameter is oxygen saturation and said second physiological parameter is pulse rate.

8. The monitor of claim 5, wherein said first physiological parameter is total hemoglobin and said second physiological parameter is plethysmograph variability index.

9. The monitor of claim 1, wherein said configurable replay display view comprises said box-and-whisker view.

10. The monitor of claim 1, wherein said configurable replay display view comprises said gauge-histogram view.

11. The monitor of claim 1, wherein said at least one communication port comprises one or more serial ports.

12. The monitor of claim 11, wherein said other data comprises data from one or more of infusion pumps, closed loop control systems, ventilator systems, blood pressure systems, or vital signs monitors.

13. The monitor of claim 1, wherein said monitor communicates with one or more of an oximetry optical sensor, an acoustic sensor, a blood pressure sensor, an NIBP sensor, a temperature sensor, or a respiration sensor.

14. The monitor of claim 1, wherein a change in color or a highlight in at least a portion of said configurable replay display view indicates a changing severity of a condition of the monitored patient based on the determined first data indicative of said first physiological parameter.

15. The monitor of claim 1, wherein said at least one communication port comprises one or more channel ports.

16. The monitor of claim 15, wherein said other data comprises data responsive to one or more of depth of consciousness, brain oxygenation, or organ oxygenation.

17. The monitor of claim 1, wherein said configurable replay display view comprises said index view.

18. The monitor of claim 1, wherein the touchscreen display is responsive to said one or more of said plurality of processors to present replayed and real-time data concurrently.

19. A method of monitoring physiological parameters of a patient using a medical monitor including a configurable replay display, said monitor configured to analyze and present indicia reflective of physiological parameters of the patient in real time and replayed for stored data, said parameters including oxygen saturation, the method comprising:

receiving, at at least one sensor port, a first signal responsive to light attenuated by tissue of a wearer of at least one noninvasive sensor, wherein a housing of a medical monitor positions said at least one sensor port;

receiving at at least one communication port positioning by said housing, other data responsive to physiology of said wearer from devices separate and different from said medical monitor;

processing, with one or more of a plurality of processors of a processing system, said received first signal to generate first data indicative of a first physiological parameter, said housing enclosing said processing system, said first data including at least one waveform, measurement values of said physiological parameter, and when applicable, visual alarms associated with said measurement values, one or more of said plurality of processors configured to receive said other data and timewise synchronize the first data with said other data, wherein said first data and said other data need not be determining measurement values at the same rate, wherein one or more of said plurality of processors are configured to process said first data or said other data or both, to create virtual channel data including non-measured parameter data resulting from processing said first data or said channel data or both;

causing a touchscreen display to present a configurable replay display view, in response to one or more of said plurality of processors, said housing positioning said touchscreen display, said configurable replay display view including a plurality of presentation views, said plurality of presentation views being user-selectable to include a heat map view and two or more of a box-and-whisker view, a distribution view, a histogram view, an index view, or a gage histogram view;

storing, in a data storage device, said first data, said virtual channel data, and said other data for use during a replay process, said housing enclosing said data storage device; and replaying, on said touchscreen display responsive to at least a plurality of finger control gestures made while in contact with said touchscreen display and within the configurable replay display first view, past values of said stored first data, said virtual channel data, and when selected, said other data, formatted into said configurable replay display view including selected ones of said plurality of presentation views;

said replaying including automatically formatting said past values according to axis alterations in response to said control gestures made within said configurable replay display view.

20. The method of claim 19, wherein said heat map view is configured to present:

a relationship between said first physiological parameter and a second physiological parameter and to identify an area in said heat map view in which said second data is concentrated.

21. The method of claim 20, wherein said heat map view is configured to identify a first area associated with a first concentration of said second data and a second area associated with a second concentration of said second data, wherein said first area is presented in a first color and said second area is presented in a second color.

22. The method of claim 19, comprising causing an entirety of said replayed first data, said virtual channel data, and when selected, said other data to be presented for a duration that is shorter than when said first data, said virtual channel data, and said other data was presented in real time.

23. The method of claim 19, comprising causing an entirety of said replayed first data, said virtual channel data, and when selected, said other data to be presented for a duration that is longer than when said first data, said virtual channel data, and said other data was presented in real time.

24. The method of claim 19, comprising causing said replayed first data, said virtual channel data, and when selected, said other data to be presented for a duration that is equal to when said first data, said virtual channel data, and said other data was presented in real time.

25. The method of claim 19, wherein said configurable replay display view comprises said box-and-whisker view.

26. The method of claim 19, wherein said configurable replay display view comprises said gauge-histogram view.

27. The method of claim 19, wherein a change in color or a highlight in at least a portion of said configurable replay display view indicates a changing severity of a condition of the monitored patient based on the determined first data indicative of said first physiological parameter.

28. The method of claim 19, wherein said at least one communication port comprises one or more channel ports.

29. The method of claim 28, wherein said other data comprises data responsive to one or more of depth of consciousness, brain oxygenation, or organ oxygenation.

30. The method of claim 19, wherein said at least one communication port comprises one or more serial ports.

31. The method of claim 30, wherein said other data comprises data from one or more of infusion pumps, closed loop control systems, ventilator systems, blood pressure systems, or vital signs monitors.

32. The method of claim 19, wherein said configurable replay display view comprises said index view.

33. The method of claim 19, comprising causing replayed and real-time data to be presented concurrently.

* * * * *